US011793896B2

(12) United States Patent
Brockschmidt, Jr. et al.

(10) Patent No.: US 11,793,896 B2
(45) Date of Patent: Oct. 24, 2023

(54) PORTABLE SANITIZING SYSTEMS AND METHODS

(71) Applicant: THE BOEING COMPANY, Chicago, IL (US)

(72) Inventors: Arthur Edward Brockschmidt, Jr., Renton, WA (US); Kevin S. Callahan, Everett, WA (US); Jamie J. Childress, Mercer Island, WA (US); Michael Kipling Klein, Bothell, WA (US); Douglas Alan Brown, Edmonds, WA (US); Christopher Edward Plass, Snohomish, WA (US); Teresa A. King, Bothell, WA (US)

(73) Assignee: THE BOEING COMPANY, Chicago, IL (US)

(*) Notice: Subject to any disclaimer, the term of this patent is extended or adjusted under 35 U.S.C. 154(b) by 310 days.

(21) Appl. No.: 17/026,417

(22) Filed: Sep. 21, 2020

(65) Prior Publication Data
US 2022/0023458 A1    Jan. 27, 2022

Related U.S. Application Data

(60) Provisional application No. 63/054,985, filed on Jul. 22, 2020.

(51) Int. Cl.
*A61L 2/10*    (2006.01)
*A61L 2/26*    (2006.01)

(52) U.S. Cl.
CPC ............ *A61L 2/10* (2013.01); *A61L 2/26* (2013.01); *A61L 2202/11* (2013.01); *A61L 2202/16* (2013.01); *A61L 2202/25* (2013.01)

(58) Field of Classification Search
CPC .......... A61L 2/10; A61L 2/26; A61L 2202/11; A61L 2202/16; A61L 2202/25
See application file for complete search history.

(56) References Cited

U.S. PATENT DOCUMENTS

| 7,888,657 | B1 | 2/2011 | Zadro |
| 9,095,633 | B1* | 8/2015 | Dayton ..................... A61L 2/10 |
| 2014/0039582 | A1* | 2/2014 | Wilson ................. A61L 2/0047 |
| | | | 607/90 |

(Continued)

FOREIGN PATENT DOCUMENTS

| CN | 111920977 | 11/2020 |
| CN | 114712533 | 7/2022 |
| EP | 4011403 | 6/2022 |

OTHER PUBLICATIONS

U.S. Appl. No. 17/016,466, filed Sep. 10, 2020.

(Continued)

*Primary Examiner* — Sean E Conley
(74) *Attorney, Agent, or Firm* — The Small Patent Law Group LLC; Joseph M. Butscher

(57) ABSTRACT

A portable sanitizing system, comprising a wand assembly including a sanitizing head having an ultraviolet (UV) lamp. A case assembly includes a cover coupled to a main body. The cover is configured to be moved between an open position that exposes a storage chamber and a closed position. The wand assembly is configured to be stored in the storage chamber when not in use and removed from the storage chamber to disinfect one or more components with UV light emitted by the UV lamp.

33 Claims, 18 Drawing Sheets

(56) References Cited

U.S. PATENT DOCUMENTS

2020/0215214 A1    7/2020  Rosen
2022/0105212 A1    4/2022  Callahan

OTHER PUBLICATIONS

U.S. Appl. No. 29/735,235, filed May 19, 2020.
U.S. Appl. No. 17/039,011, filed Sep. 30, 2020.
U.S. Appl. No. 17/026,414, filed Sep. 21, 2020.
U.S. Appl. No. 17/020,942, filed Sep. 15, 2020.
U.S. Appl. No. 16/987,514, filed Aug. 7, 2020.
U.S. Appl. No. 17/104,628, filed Nov. 25, 2020.
U.S. Appl. No. 16/987,647, filed Aug. 7, 2020.
U.S. Appl. No. 17/020,951, filed Sep. 15, 2020.
"Honeywell UV Treatment System," https://aerospace.honeywell.com/en/learn/products/cabin/uv-cabin-system.
U.S. Appl. No. 17/026,435, filed Sep. 21, 2020.
U.S. Appl. No. 17/022,392, filed Sep. 16, 2020.
Blithe0815: "Unboxing Portable UV Sterilizer," Jul. 7, 2020, pp. 1-8, XP05587088, retrieved from Internet: URL: https://www.youtube.com/watch?v=UKewqn1H5nl.
Extended European Search Report for EP 21186185.1-1012, dated Dec. 20, 2021.
Communication for EP 21186185.1-1012, dated Mar. 29, 2023.

\* cited by examiner

PORTABLE SANITIZING SYSTEMS AND METHODS

RELATED APPLICATIONS

This application relates to and claims priority benefits from U.S. Provisional Patent Application No. 63/054,985, entitled "Portable Sanitizing Systems and Methods," filed Jul. 22, 2020.

FIELD OF THE DISCLOSURE

Embodiments of the present disclosure generally relate to sanitizing systems, such as may be used to sanitize structures and areas within vehicles, such as commercial aircraft.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light. In order to sanitize a surface of a structure, a known UV light sterilization method emits a broad spectrum USC light onto the structure.

Further, known UV light sanitizing systems are typically large, bulky, and often require fixed, stationary infrastructure.

SUMMARY OF THE DISCLOSURE

A need exists for a system and a method for efficiently sterilizing surfaces within an internal cabin of a vehicle. Further, a need exists for a mobile, compact, easy-to-use, and safe system and method for using UV light to sterilize surfaces within an internal cabin.

With those needs in mind, certain embodiments of the present disclosure provide a portable sanitizing system including a wand assembly including a sanitizing head having an ultraviolet (UV) lamp. A case assembly includes a cover coupled to a main body. The cover is configured to be moved between an open position that exposes a storage chamber and a closed position. The wand assembly is configured to be stored in the storage chamber when not in use and removed from the storage chamber to disinfect one or more components with UV light emitted by the UV lamp.

In at least one embodiment, the UV lamp is configured to emit the UV light having a wavelength between 200 nm-230 nm to disinfect a surface. For example, the UV lamp is configured to emit the UV light having a wavelength of 222 nm to disinfect a surface.

In at least one other embodiment, the UV lamp is configured to emit the UV light having a wavelength between 230 nm-280 nm to disinfect a surface. For example, the UV lamp is configured to emit the UV light having a wavelength of 254 nm to disinfect a surface.

In at least one embodiment, the case assembly includes a hose retainer that is configured to secure a hose on the cover when the wand assembly is within the storage chamber and the cover is the closed position. For example, the hose retainer includes a flexible fabric sheet.

In at least one embodiment, a cooling fan is within the storage chamber. The cooling fan is configured to couple to the wand assembly through a hose. The cooling fan is configured to deliver cooling air to the wand assembly through the hose.

In at least one embodiment, one or more batteries are within the storage chamber.

In at least one embodiment, a power supply is within the storage chamber. The power supply is configured to couple to the wand assembly through a power cord.

In at least one embodiment, a hole is formed through a portion of the case assembly. The hole is configured to allow one or both of a portion of a hose or a portion of a power cord to pass.

The wand assembly may include an activation trigger secured to an underside of a main beam of a handle. Further, the wand assembly may include a cooling manifold that is configured to deliver cooling air to the UV lamp.

Certain embodiments of the present disclosure provide a portable sanitizing method, comprising moving a cover of a case assembly between an open position that exposes a storage chamber and a closed position; storing a wand assembly including a sanitizing head having an ultraviolet (UV) lamp in the storage chamber when not in use; and removing the wand assembly from the storage chamber to disinfect one or more components with UV light emitted by the UV lamp.

DETAILED DESCRIPTION OF THE DISCLOSURE

Figure 1:
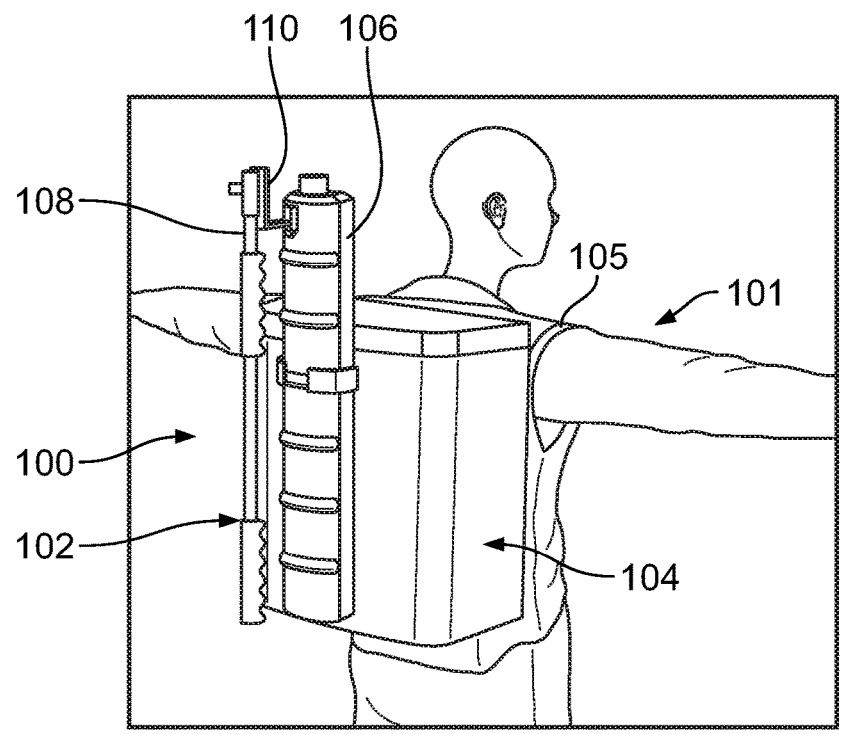
FIG. 1 illustrates a perspective view of a portable sanitizing system worn by an individual, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

In at least one embodiment, a sanitizing system is a portable system for disinfecting surfaces. The sanitizing system includes a wand assembly and a rolling case assembly. The wand assembly includes a UV lamp, such as a 222 nm UV lamp. A cooling manifold is configured to allow air to blow across a bulb of the UV lamp. The wand assembly may also include a two piece reflector, a master power switch, and a trigger switch to illuminate the UV lamp.

In at least one embodiment, the rolling case assembly includes a hard plastic case with a hinged upper lid portion, a lower body portion, two casters, and an extension handle to facilitate carrying and rolling the cart. The lower body portion contains a power supply, one or more batteries (such as three rechargeable batteries), a power cord for powering the power supply, a cooling fan, and a space to store the wand assembly when not in use. The wand assembly and the rolling case assembly are connected with a vent hose that contains power wiring and transmits cooling air from the cooling fan to the wand housing. The upper lid portion contains a fabric cover to secure the vent hose to the upper lid portion for storage.

During use, the rolling case assembly may be placed away from the area being disinfected, thereby allowing the operator to transport only the wand assembly to the area, and facilitating movement and operation in tight or confined spaces. The wand assembly may include a 300 watt, 222 nm UV lamp, optional ranging lights, a cooling manifold running the length of the housing to blow air out across the bulb to cool the bulb, a two piece reflector positioned in the housing on either side of the cooling manifold to direct light waves, mounts to secure the lamp to the housing, a master power switch on the handle to turn on the system, and a trigger switch on the wand handle that illuminates the lamp when depressed. The reflector may be made out of Teflon or an aluminum sheet, which will enable the reflector to provide electromagnetic shielding. The bulb may be attached to the wand housing with wire straps or bands, which may be positioned on top of Teflon tape and dry woven fiberglass that serve as a cushion between the strap and the glass bulb. The housing for the wand assembly may be approximately (such as +/−0.02 inches) 4 inches wide, 20 inches long, and made out of materials such as fiberglass or reinforced plastic.

In at least one embodiment, the lower body portion of the case contains a power supply mounted on an interior portion, rechargeable batteries, a power cord for connecting electrical power to the power supply, a cooling fan with an outlet through the wall of the lower portion of the case to the hose that connects the wand assembly to the rolling case assembly, at least one latch on the exterior of the lid to secure the upper lid to the lower body portion of the case, and a space to store the wand housing inside the lower body portion when not in use. The rolling case assembly is configured such that the batteries provide power to the UV lamp if the power cord is not plugged into a power outlet. If the power cord is plugged into a power outlet, relays switch over to accept electrical power. In addition, the power cord also supplies power to charge the batteries. A vent hose connects the wand assembly to the rolling case assembly. The vent hose blows the air from the cooling fan in the case through the vent hose and through the cooling manifold in the wand housing to cool the lamp. In addition, the vent hose contains the wiring that is routed from the power supply in the case to the wand assembly to provide power to the UV lamp. The rechargeable batteries may be removed from the backpack or case assembly for charging, or may remain in the backpack to charge as a system. The power cord may be stowed inside the case during transit and battery use. The power cord will exit through a semi-circular hole in the lower body portion of the case when the wand is in use.

When the case is in the closed position, the excess vent hose may be coiled on top of the exterior of the upper lid portion, and a nylon or fabric cover that is attached to one side of the lid exterior is pulled over the hose and secured to the other side of the upper lid portion with buckles or other type mechanical fasteners to secure the cover to the upper lid portion. The lower body portion of the case has a semi-circular shaped opening so that the vent house may be placed in the opening when the wand housing is stored in the case to allow the case to fully close. Additionally, the semi-circular hole will also allow intake air to be drawn into the wand cooling fan even if the case is closed during operation.

FIG. 1 illustrates a perspective view of a portable sanitizing system 100 worn by an individual 101, according to an embodiment of the present disclosure. The portable sanitizing system 100 includes a wand assembly 102 coupled to a backpack assembly 104 that is removably secured to the individual through a harness 105. The wand assembly 102 includes a sanitizing head 106 coupled to a handle 108. In at least one embodiment, the sanitizing head 106 is moveably coupled to the handle 108 through a coupler 110.

In at least one other embodiment, the portable sanitizing system 100 may not be worn by the individual 101. For example, the portable sanitizing system 100 may include a case assembly that is configured to be opened and closed. The case assembly may store the wand assembly 102 when not in use. The case assembly may be opened to allow the wand assembly 102 to be removed and operated.

As shown in FIG. 1, the wand assembly 102 is in a stowed position. In the stowed position, the wand assembly 102 is removably secured to a portion of the backpack assembly 104, such as through one or more tracks, clips, latches, belts, ties, and/or the like.

In at least one other embodiment, the wand assembly 102 is stored within a case assembly in a stowed position. For example, the wand assembly 102 in the stowed position is contained within a closed case assembly. The case assembly may be opened to allow the wand assembly 102 to be removed and deployed.

Figure 2:
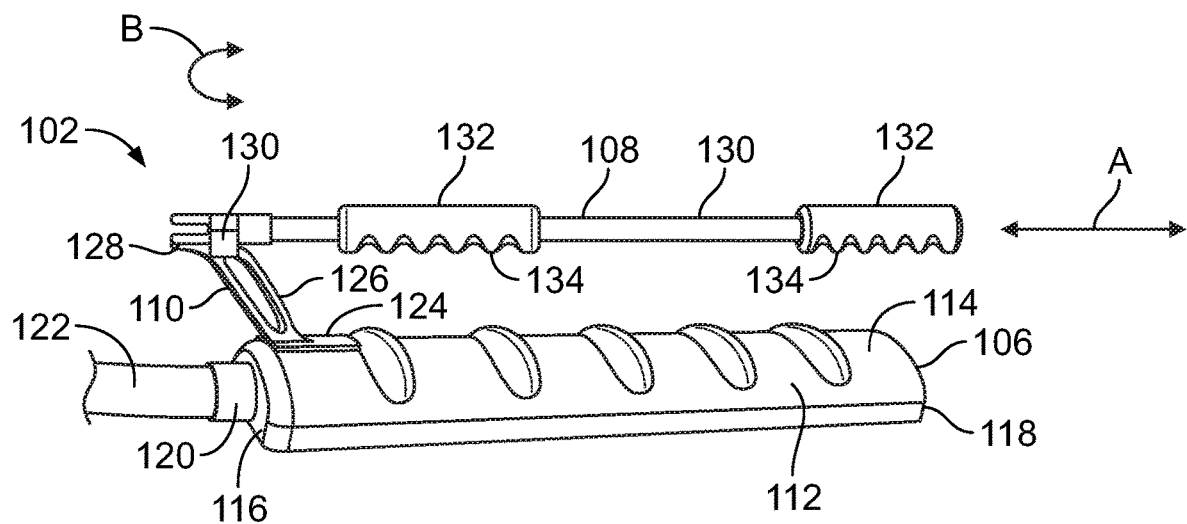
FIG. 2 illustrates a perspective lateral top view of a wand assembly, according to an embodiment of the present disclosure.

FIG. 2 illustrates a perspective lateral top view of the wand assembly 102, according to an embodiment of the present disclosure. The sanitizing head 106 couples to the handle 108 through the coupler 110. The sanitizing head 106 includes a shroud 112 having an outer cover 114 that extends from a proximal end 116 to a distal end 118. As described herein, the shroud 112 contains a UV lamp.

Optionally, the wand assembly 102 may include the sanitizing head 106 connected to a fixed handle. Further, the wand assembly 102 may be sized and shaped differently than shown.

A port 120 extends from the proximal end 116. The port 120 couples to a hose 122, which, in turn, couples to the backpack assembly 104 (shown in FIG. 1). The hose 122 contains electrical cords, cables, wiring, or the like that couples a power source or supply (such as one or more batteries) within the backpack assembly 104 (shown in FIG. 1) to a UV lamp 140 within the shroud 112. Optionally, electrical cords, cables, wiring, or the like may be outside of the hose 122. In at least one embodiment, the hose 122 also contains an air delivery line, such as an air tube) that fluidly couples an internal chamber of the shroud 112 to an air blower, vacuum generator, air filters, and/or the like within the backpack assembly 104.

The coupler 110 is secured to the outer cover 114 of the shroud 112, such as proximate to the proximal end 116. The coupler 110 may include a securing beam 124 secured to the outer cover 114, such as through one or more fasteners, adhesives, and/or the like. An extension beam 126 outwardly extends from the securing beam 124, thereby spacing the handle 108 from the shroud 112. A bearing assembly 128 extends from the extension beam 126 opposite from the securing beam 124. The bearing assembly 128 includes one or more bearings, tracks, and/or the like, which allow the handle 108 to linearly translate relative to the coupler 110 in the directions of arrows A, and/or pivot about a pivot axle in the directions of arc B. Optionally, the securing beam 124 may include a bearing assembly that allows the sanitizing head 106 to translate in the directions of arrows A, and/or rotate (for example, swivel) in the directions of arc B in addition to, or in place of, the handle 108 being coupled to the bearing assembly 128 (for example, the handle 108 may be fixed to the coupler 110).

In at least one other embodiment, the wand assembly 102 does not include the coupler 110. Instead, the handle 108 may be fixed to the shroud 112, for example.

In at least one embodiment, the handle 108 includes a rod, pole, beam, or the like 130, which may be longer than the shroud 112. Optionally, the rod 130 may be shorter than the shroud 112. One or more grips 132 are secured to the rod 130. The grips 132 are configured to be grasped and held by an individual. The grips 132 may include ergonomic tactile features 134.

Optionally, the wand assembly 102 can be sized and shaped differently than shown. For example, in at least one example, the handle 108 can be fixed in relation to the shroud 112. Further, the handle 108 may not be configured to move relative to itself and/or the shroud 112. For example, the handle 108 and the shroud 112 can be integrally molded and formed as a single unit.

Figure 3:
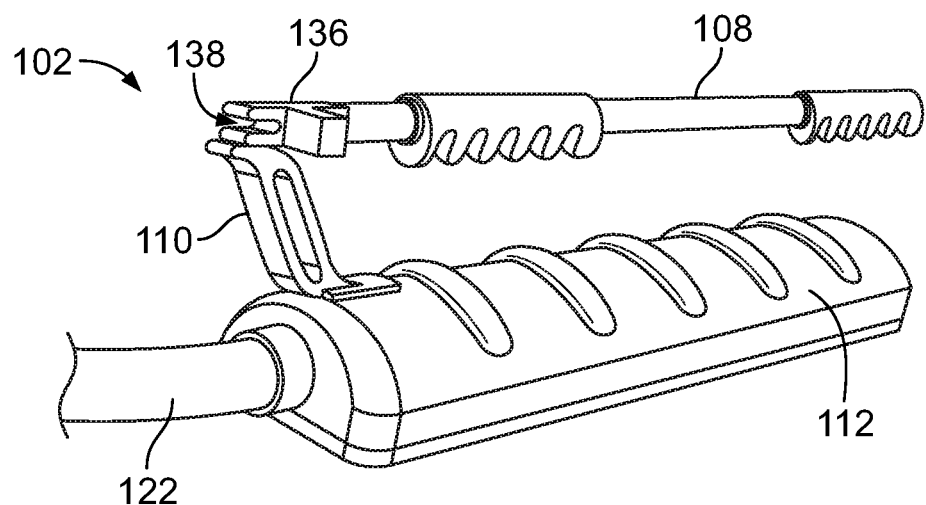
FIG. 3 illustrates a perspective rear view of the wand assembly of FIG. 2.
Figure 4:
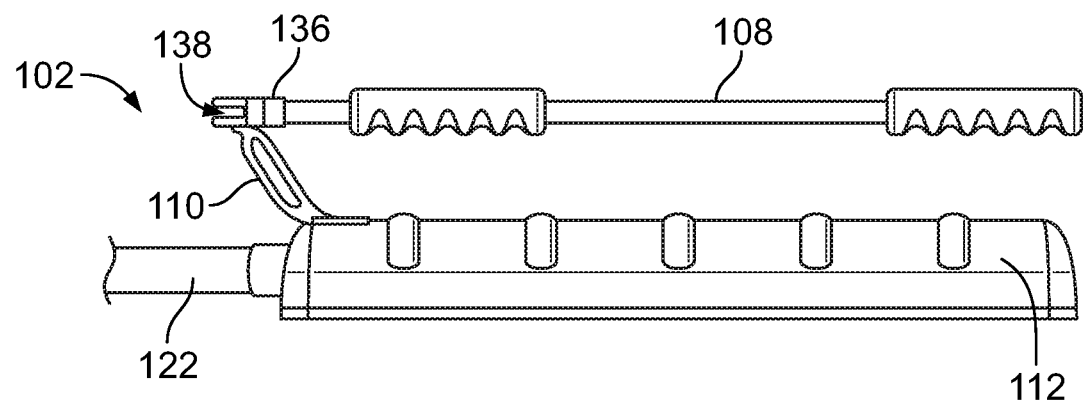
FIG. 4 illustrates a perspective lateral view of the wand assembly of FIG. 2.

FIG. 3 illustrates a perspective rear view of the wand assembly 102 of FIG. 2. FIG. 4 illustrates a perspective lateral view of the wand assembly 102 of FIG. 2. Referring to FIGS. 3 and 4, the handle 108 may pivotally couple to the coupler 110 through a bearing 136 having a pivot axle 138 that pivotally couples the handle 108 to the coupler 110. The handle 108 may further be configured to linearly translate into and out of the bearing 136. For example, the handle 108 may be configured to telescope in and out. Optionally, or alternatively, in at least one embodiment, the handle 108 may include a telescoping body that allows the handle 108 to outwardly extend and inwardly recede. In at least one other embodiment, the handle 108 may not be configured to move, extend, retract, or the like relative to the shroud 112.

Figure 5:
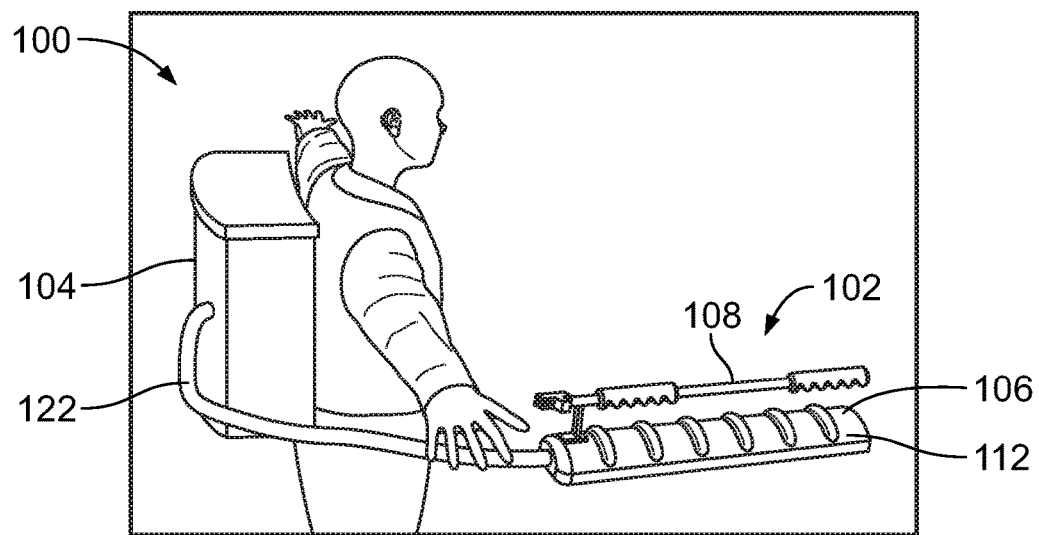
FIG. 5 illustrates a perspective view of the portable sanitizing system in a compact deployed position, according to an embodiment of the present disclosure.

FIG. 5 illustrates a perspective view of the portable sanitizing system 100 in a compact deployed position, according to an embodiment of the present disclosure. The wand assembly 102 is removed from the backpack assembly 104 (as shown in FIG. 1) into the compact deployed position, as shown in FIG. 5. The hose 122 connects the wand assembly 102 to the backpack assembly 104. In the compact deployed position, the sanitizing head 106 is fully retracted in relation to the handle 108.

Figure 6:
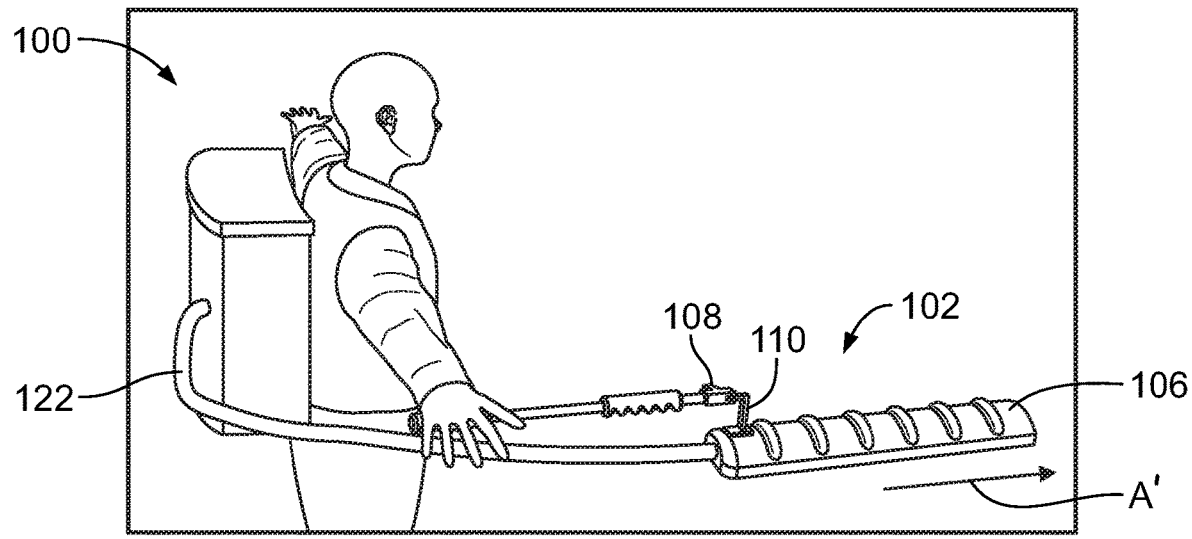
FIG. 6 illustrates a perspective view of the portable sanitizing system having a sanitizing head in an extended position, according to an embodiment of the present disclosure.

FIG. 6 illustrates a perspective view of the portable sanitizing system 100 having the sanitizing head 106 in an extended position, according to an embodiment of the present disclosure. In order to extend the sanitizing head 106 relative to the handle 108, the sanitizing head 106 is outwardly slid relative to the handle 108 in the direction of arrow A' (or the handle 108 is rearwardly slid relative to the sanitizing head 106). As noted, the sanitizing head 106 is able to linearly translate in the direction of arrow A' relative to the handle 108 via the coupler 110. The outward extension of the sanitizing head 106, as shown in FIG. 6, allows for the portable sanitizing system 100 to easily reach distant areas. Alternatively, the sanitizing head 106 may not linearly translate relative to the handle 108.

Figure 7:
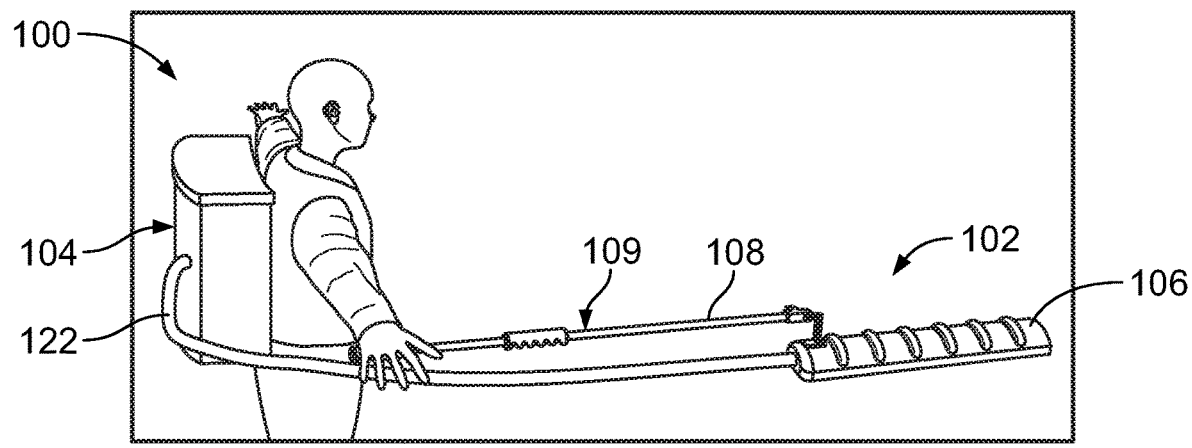
FIG. 7 illustrates a perspective view of the portable sanitizing system having the sanitizing head in an extended position and a handle in an extended position, according to an embodiment of the present disclosure.

FIG. 7 illustrates a perspective view of the portable sanitizing system 100 having the sanitizing head 106 in an extended position and the handle 108 in an extended position, according to an embodiment of the present disclosure. To reach even further, the handle 108 may be configured to linearly translate, such as through a telescoping portion, to allow the sanitizing head 106 to reach further outwardly. Alternatively, the handle 108 may not be configured to extend and retract.

In at least one embodiment, the handle 108 may include a lock 109. The lock 109 is configured to be selectively operated to secure the handle 108 into a desired extended (or retracted) position.

Figure 8:
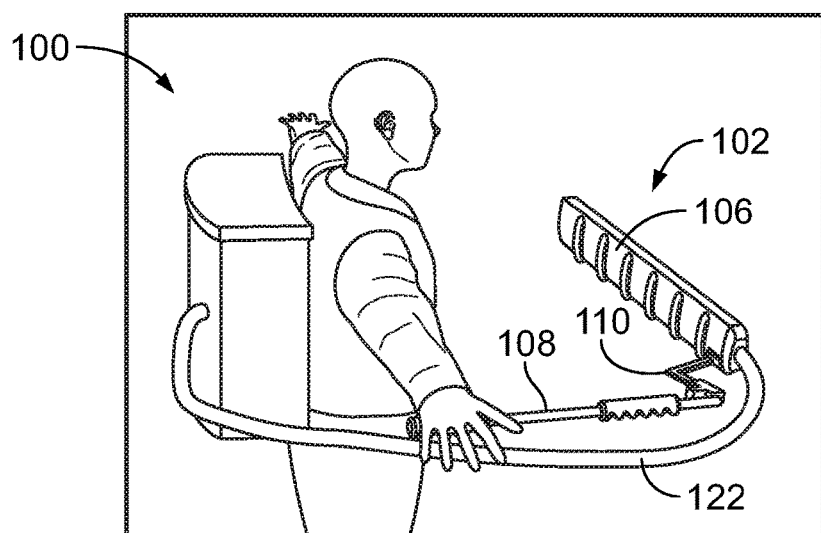
FIG. 8 illustrates a perspective view of the portable sanitizing system having the sanitizing head rotated in relation to the handle, according to an embodiment of the present disclosure.

FIG. 8 illustrates a perspective view of the portable sanitizing system 100 having the sanitizing head 106 rotated in relation to the handle 108, according to an embodiment of the present disclosure. As noted, the sanitizing head 106 is configured to rotate relative to the handle 108 via the coupler 110. Rotating the sanitizing head 106 relative to the handle 108 allows the sanitizing head 106 to be moved to a desired position, and sweep or otherwise reach into areas that would otherwise be difficult to reach if the sanitizing head 106 was rigidly fixed to the handle 108. Alternatively, the sanitizing head 106 may not be rotatable relative to the handle 108.

Figure 9:
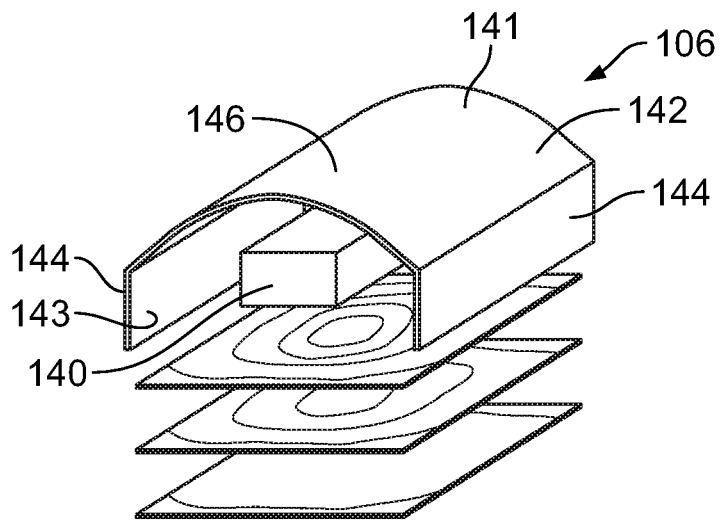
FIG. 9 illustrates a perspective end view of a UV lamp and a reflector of the sanitizing head, according to an embodiment of the present disclosure.

FIG. 9 illustrates a perspective end view of a UV lamp 140 and a reflector 142 of the sanitizing head 106, according to an embodiment of the present disclosure. The UV lamp 140 and the reflector 142 are secured within the shroud 112 (shown in FIG. 2, for example) of the sanitizing head 106. In at least one embodiment, the reflector 142 is secured to an underside 141 of the shroud 112, such as through one or more adhesives. As another example, the reflector 142 is an integral part of the shroud 112. For example, the reflector 142 may be or otherwise provide the underside 141 of the shroud 112. The reflector 142 provides a reflective surface 143 (such as formed of Teflon, a mirrored surface, and/or the like) that is configured to outwardly reflect UV light emitted by the UV lamp 140. In at least one example, shroud 112 may be or include a shell formed of fiberglass, and the reflector 142 may be formed of Teflon that provides a 98% reflectivity. In at least one embodiment, the reflector 142 may be a multi-piece reflector.

The reflector 142 may extend along an entire length of the underside 141 of the shroud 112. Optionally, the reflector 142 may extend along less than an entire length of the underside 141 of the shroud 112.

The UV lamp 140 may extend along an entire length (or along substantially the entire length, such as between the ends 116 and 118). The UV lamp 140 is secured to the reflector 142 and/or the shroud 112 through one or more mounts, such as brackets, for example. The UV lamp 140 includes one or more UV light emitters, such as one more bulbs, light emitting elements (such as light emitting diodes), and/or the like. In at least one embodiment, the UV lamp 140 is configured to emit UV light in the far UV spectrum, such as at a wavelength between 200 nm-230 nm. In at least one embodiment, the UV lamp 140 is configured to emit UV light having a wavelength of 222 nm. For example, the UV lamp 140 may be or include a 300 W bulb that is configured to emit UV light having a wavelength of 222 nm. Alternatively, the UV lamp 140 may be configured to emit UV light in other portions of the UV spectrum, such as the USC spectrum.

As shown, the reflector 142 includes flat, upright side walls 144 connected together through an upper curved wall 146. The upper curved wall 146 may be bowed outwardly away from the UV lamp 140. For example, the upper curved wall 146 may have a parabolic cross-section and/or profile.

It has been found that the straight, linear side walls 144 provide desired reflection and/or focusing of UV light emitted from the UV lamp 140 toward and onto a desired location. Alternatively, the side walls 144 may not be linear and flat.

Figure 10:
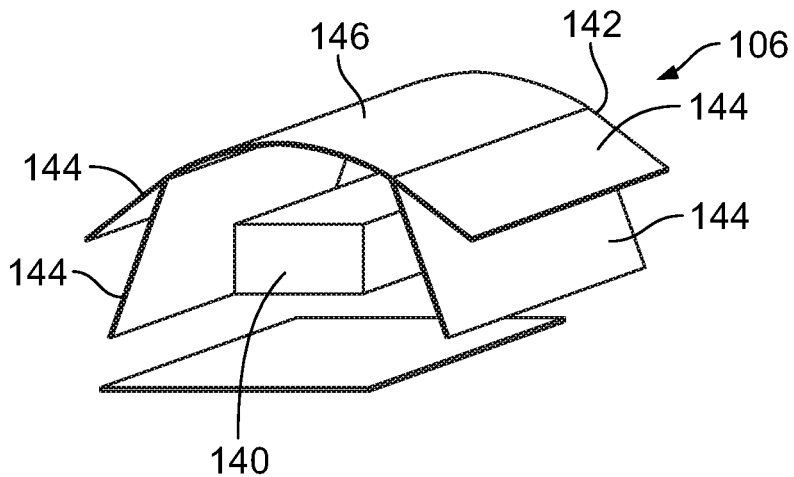
FIG. 10 illustrates a perspective end view of a UV lamp and a reflector of the sanitizing head, according to an embodiment of the present disclosure.

FIG. 10 illustrates a perspective end view of the UV lamp 140 and a reflector 142 of the sanitizing head, according to an embodiment of the present disclosure. The reflector 142 shown in FIG. 10 is similar to the reflector 142 shown in FIG. 9, except that the side walls 144 may outwardly cant from the upper curved wall 146.

Figure 11:
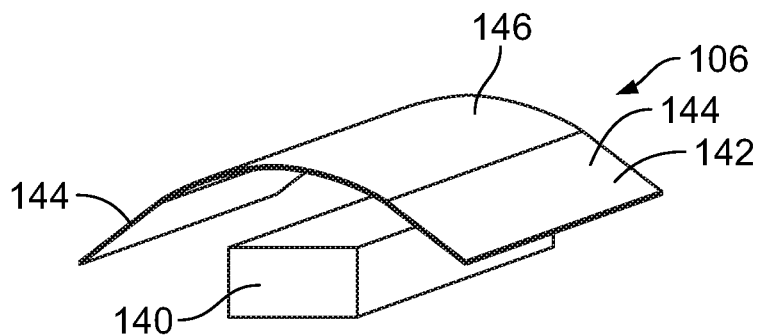
FIG. 11 illustrates a perspective end view of a UV lamp and a reflector of the sanitizing head, according to an embodiment of the present disclosure.

FIG. 11 illustrates a perspective end view of the UV lamp 140 and the reflector 142 of the sanitizing head, according to an embodiment of the present disclosure. In this embodiment, the side walls 144 may be curved according to the curvature of the upper curved wall 146.

Figure 12:
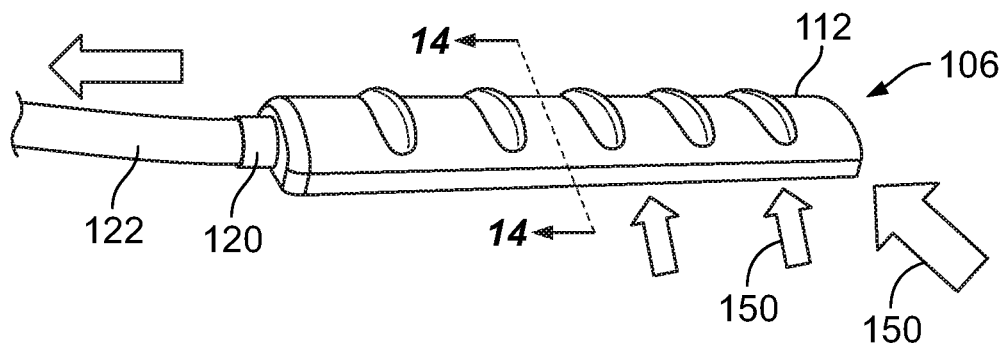
FIG. 12 illustrates a perspective top view of the sanitizing head.
Figure 13:
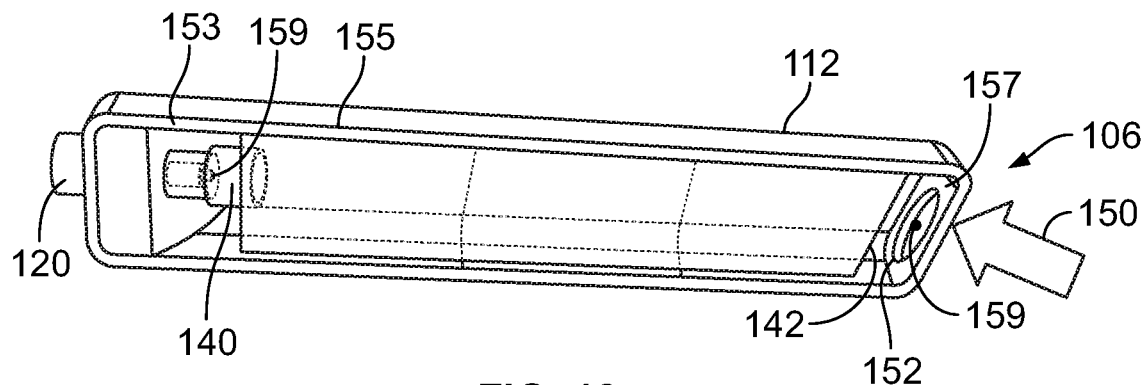
FIG. 13 illustrates a perspective bottom view of the sanitizing head.
Figure 14:
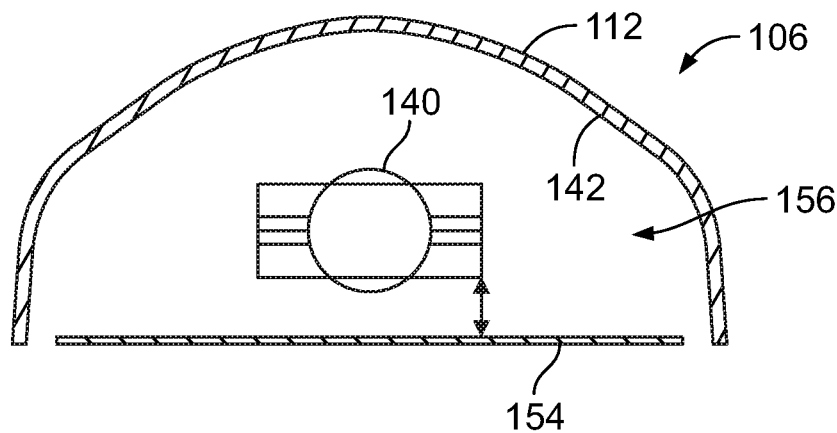
FIG. 14 illustrates an axial cross-sectional view of the sanitizing head through line 14-14 of FIG. 12.

FIG. 12 illustrates a perspective top view of the sanitizing head 106. FIG. 13 illustrates a perspective bottom view of the sanitizing head 106. FIG. 14 illustrates an axial cross-sectional view of the sanitizing head 106 through line 14-14 of FIG. 12. Referring to FIGS. 12-14, air 150 is configured to be drawn into the sanitizing head 106 through one or more openings 152 (or simply an open chamber) of the shroud 112. The air 150 is drawn into the sanitizing head 106, such as via a vacuum generator within the backpack assembly 104 (shown in FIG. 1). The air 150 is drawn into the shroud 112, and cools the UV lamp 140 as it passes over and around the UV lamp 140. The air 150 passes into the port 120 and into the hose 122, such as within an air tube within the hose 122. The air 150 not only cools the UV lamp 140, but also removes ozone, which may be generated by operation of the UV lamp 140, within the shroud 112. The air 150 may be drawn to an air filter, such as an activated carbon filter, within the backpack assembly 104.

In at least one embodiment, the portable sanitizing system 100 may also include an alternative ozone mitigation system. As an example, the ozone mitigation system may be disposed in the shroud 112 or another portion of the system, and may include an inert gas bath, or a face inert gas system, such as in U.S. Pat. No. 10,232,954.

Referring to FIG. 13, in particular, a bumper 153 may be secured to an exposed lower circumferential edge 155 of the shroud 112. The bumper 153 may be formed of a resilient material, such as rubber, another elastomeric material, open or closed cell foam, and/or the like. The bumper 153 protects the sanitizing head 106 from damage in case the sanitizing head 106 inadvertently contacts a surface. The bumper 153 also protects the surface from damage.

The openings 152 may be spaced around the lower surface of the shroud 112 such that they do not provide a direct view of the UV lamp 140. For example, the openings 152 may be positioned underneath portions that are spaced apart from the UV lamp 140.

Referring to FIG. 14, in particular, the sanitizing head 106 may include a cover plate 154 below the UV lamp 140. The cover plate 154 may be formed of glass, for example, and may be configured to filter UV light emitted by the UV lamp 140. The UV lamp 140 may be secured within an interior chamber 156 defined between the reflector 142 and the cover plate 154. In at least one embodiment, the cover plate 154 is or otherwise includes a far UV band pass filter. For example, the cover plate 154 may be a 222 nm band pass filter that filters UV light emitted by the UV lamp 140 to a 222 nm wavelength. As such, UV light that is emitted from the sanitizing head 106 may be emitted at a wavelength of 222 nm.

Referring to FIGS. 13 and 14, a rim 157 (such as a 0.020" thick Titanium rim) may connect the cover plate 154 to the shroud 112. The rim 157 may distribute impact loads therethrough and/or therearound.

In at least one embodiment, ranging light emitting diodes (LEDs) 159 may be disposed proximate to ends of the UV lamp 140. The ranging LEDs 159 may be used to determine a desired range to a structure that is to be sanitized, for example. In at least one embodiment, the ranging LEDs 159 may be disposed on or within the rim 157 and/or the cover plate 154. As another example, the sanitizing head 106 may be configured for range guidance, as disclosed in U.S. Provisional Application No. 63/027,869, which was filed May 20, 2020.

Figure 15:
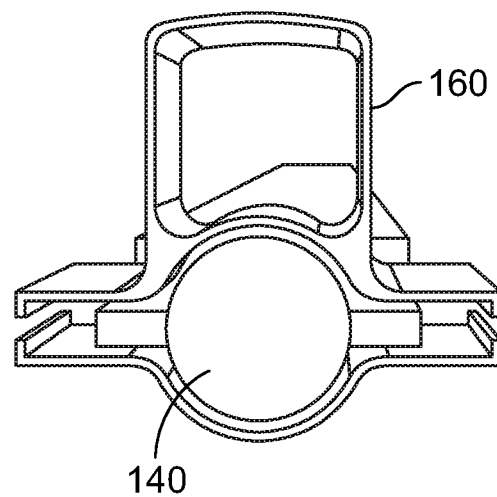
FIG. 15 illustrates a perspective end view of the UV lamp secured to a mounting bracket, according to an embodiment of the present disclosure.

FIG. 15 illustrates a perspective end view of the UV lamp 140 secured to a mounting bracket or clamp 160, according to an embodiment of the present disclosure. Each end of the UV lamp 140 may be coupled to mounting bracket or clamp 160, which secures the UV lamp 140 to the shroud 112 (shown in FIGS. 12-14). A buffer, such as a thin (for example, 0.040") sheet of silicon may be disposed between the end of the UV lamp 140 and the bracket 160. Optionally, the UV lamp 140 may be secured to the shroud 112 through brackets or clamps that differ in size and shape than shown. As another example, the UV lamp 140 may be secured to the shroud 112 through adhesives, fasteners, and/or the like.

Figure 16:
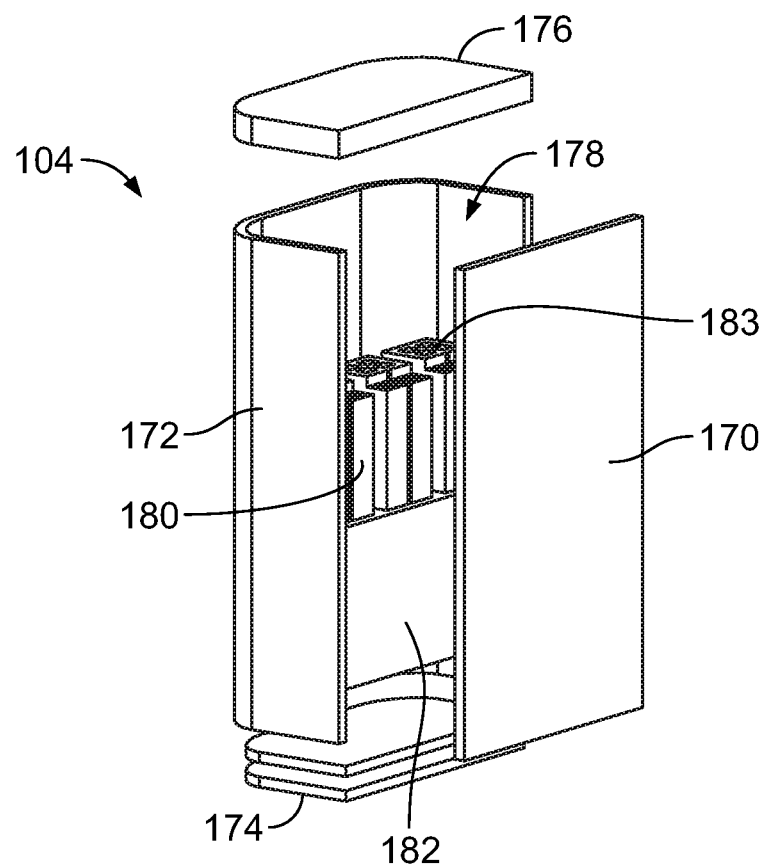
FIG. 16 illustrates a perspective exploded view of a backpack assembly, according to an embodiment of the present disclosure.

FIG. 16 illustrates a perspective exploded view of the backpack assembly 104, according to an embodiment of the present disclosure. The backpack assembly 104 includes a front wall 170 that couples to a rear shell 172, a base 174, and a top cap 176. An internal chamber 178 is defined between the front wall 170, the rear shell 172, the base 174, and the top cap 176. One or more batteries 180, such as rechargeable Lithium batteries, are contained within the internal chamber 178. An air generation sub-system 182 is also contained within the internal chamber 178. The air generation sub-system 182 is in fluid communication with an air tube within the hose 122 (shown in FIG. 2, for example). The air generation sub-system 182 may include an airflow device, such as a vacuum generator, an air blower, and/or the like. The airflow device is configured to generate airflow to cool the UV lamp, draw air from the sanitizing head 106 into the backpack assembly 104 and out through an exhaust, draw or otherwise remove generated ozone away from the shroud 112, and/or the like.

One or more air filters 183, such as carbon filters, are within the backpack assembly 104. The air filters 183 are in communication with the air tube or other such delivery duct or line that routes air through the hose 122 and into the backpack assembly 104. The air filters 183 are configured to filter the air that is drawn into the backpack assembly 104 from the shroud 112. For example, the air filters 183 may be configured to remove, deactivate, or otherwise neutralize ozone.

The batteries 180 and/or a power supply within the backpack assembly 104 provides operating power for the UV lamp 140 of the sanitizing head 106 (shown in FIG. 2, for example). The top wall 176 may be removably coupled to the front wall 170 and the rear shell 172. The top wall 176 may be removed to provide access to the batteries 180 (such as to remove and/or recharge the batteries), for example. Additional space may be provided within the backpack assembly 104 for storage of supplies, additional batteries, additional components, and/or the like. In at least one embodiment, the front wall 170, the rear shell 172, the base 174, and the top cap 176 may be formed of fiberglass epoxy.

Figure 17:
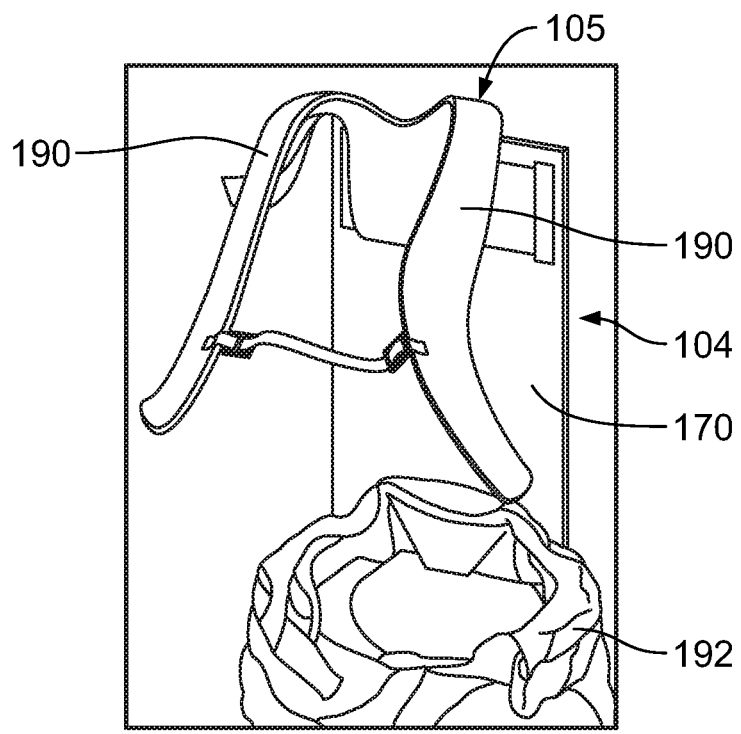
FIG. 17 illustrates a perspective front view of a harness coupled to a backpack assembly, according to an embodiment of the present disclosure.

FIG. 17 illustrates a perspective front view of the harness 105 coupled to the backpack assembly 104, according to an embodiment of the present disclosure. The harness 105 may include shoulder straps 190 and/or a waist or hip belt or strap 192, which allow the individual to comfortably wear the backpack assembly 104.

Referring to FIGS. 1-17, in operation, the individual may walk through an area wearing the backpack assembly 104. When a structure to be sanitized is found, the individual may position grasp the handle 108 and position the sanitizing head 106 as desired, such as by extending and/or rotating the sanitizing head 106 relative to the handle 108. The individual may then engage an activation button on the handle 108, for example, to activate the UV lamp 140 to emit sanitizing UV light onto the structure. As the UV lamp 140 is activated, air 150 is drawn into the shroud 112 to cool the UV lamp 140, and divert any generated ozone into the backpack assembly 104, where it is filtered by the air filters 183.

The extendable wand assembly 102 allows the sanitizing head 106 to reach distant areas, such as over an entire set of three passenger seats, from a row within an internal cabin of a commercial aircraft.

Figure 18:
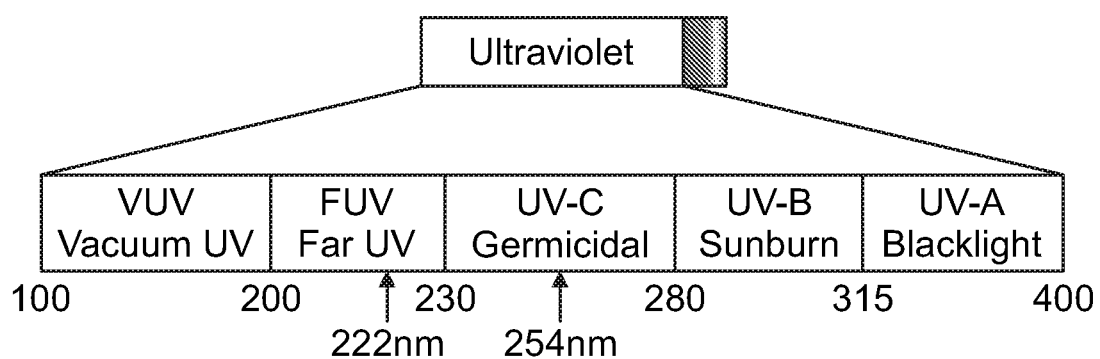
FIG. 18 illustrates an ultraviolet light spectrum.

FIG. 18 illustrates an ultraviolet light spectrum. Referring to FIGS. 1-18, in at least one embodiment, the sanitizing head 106 is configured to emit sanitizing UV light (through operation of the UV lamp 140) within a far UV spectrum, such as between 200 nm to 230 nm. In at least one embodiment, the sanitizing head 106 emits sanitizing UV light having a wavelength of 222 nm.

Figure 19:
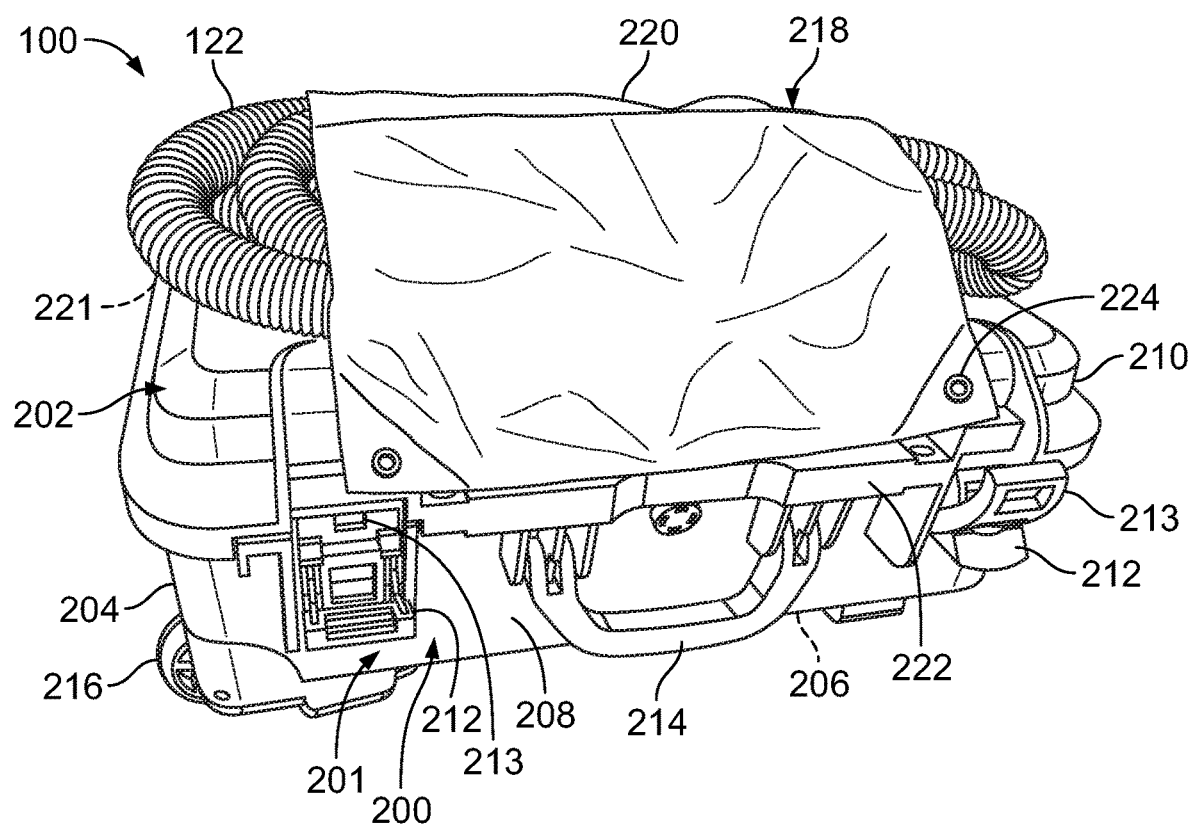
FIG. 19 illustrates a perspective view of a portable sanitizing system, according to an embodiment of the present disclosure.

FIG. 19 illustrates a perspective view of a portable sanitizing system 100, according to an embodiment of the present disclosure. The portable sanitizing system 100 includes a case assembly 200 that is configured to store the wand assembly 102 (hidden from view in FIG. 19) when the case assembly 200 is in a closed position, as shown in FIG. 19.

The case assembly 200 may be formed of plastic, for example. The case assembly 200 includes a main body 201, such as a shell, lower body portion, or the like. A cover 202, such as a lid, or upper body portion, is moveably coupled to the main body 201. For example, the cover 202 may be coupled to the main body 201 through a hinge that allows the cover 202 to be opened and closed relative to the main body 201.

The main body 201 includes a base 204 connected to a rear wall 206, lateral walls 208, and a top wall 210. The cover 202 is moveably coupled to a first lateral wall 208, such as through a hinge. One or more latches 212 are disposed on a second lateral wall 208, opposite from the first lateral wall 208. The latches 212 are configured to engage one or more reciprocal latch members 213 extending from the cover 202 to secure the cover 202 in the closed position. The latches 212 may be engaged by an individual to disengage the latch members 213 to allow the cover 202 to be pivoted into an open position.

A handle 214 is secured to the case assembly 200. For example, the handle 214 is pivotally secured to a lateral wall 208. The handle 214 is configured to be grasped by an individual so that the portable sanitizing system 100 may be carried. Optionally, the handle 214 may be secured to other portions of the case assembly 200, such as the top wall 210. In at least one embodiment, the handle 214 may be configured to retract into the case assembly 200 into a fully retracted position, and extend out of (for example, telescope out of) the case assembly 200 into a fully extended position.

Casters 216 or other such wheels may be rotatably secured to a portion of the case assembly 200. For example, two casters 216 may be rotatably secured to the base 204 proximate to the rear wall 206. An individual may tilt the case assembly 200 so that the casters 216 contact a floor. In this manner, the individual may roll the portable sanitizing system 100 via the casters 216 (and optionally through a handle in an extended position from the top wall 210). Alternatively, the case assembly 200 may not include the casters 216.

The hose 122 may outwardly extend from the case assembly 200. In the closed position, when the wand assembly 102 is in a stowed position within the case assembly 200, the hose 122 may be coiled over the cover 202. A hose retainer 218 may secure the hose 122 in place on the cover 202. For example, the hose retainer 218 may include a flexible fabric sheet 220 that is secured to a first side 221 of the cover 202, and may removably secured to an opposite second side 222 of the cover 202, such as through one or more fastening members 224, such as hooks and loops, latches, clips, and/or the like. The hose retainer 218 is configured to secure the hose 122 on the cover 202 when the wand assembly 102 is within a storage chamber of the case assembly 200 and the cover 202 is in a closed position. Alternatively, the hose 122 may be contained within a storage chamber of the case assembly 200 when the wand assembly 102 is not in use. That is, the storage chamber may be sized and shaped to also contain the hose 122 when the wand assembly 102 is also within the storage chamber and the cover 202 is in the closed position.

The wand assembly 102 within the case assembly 200 in the closed position is protected from inadvertent engagement, bumping, and the like. That is, by storing the wand assembly 102 within the case assembly 200, which is closed, when the wand assembly 102 is not in use, the portable sanitizing system 100 protects the wand assembly 102 from potential damage, and increases the useful life of the wand assembly 102.

Figure 20:
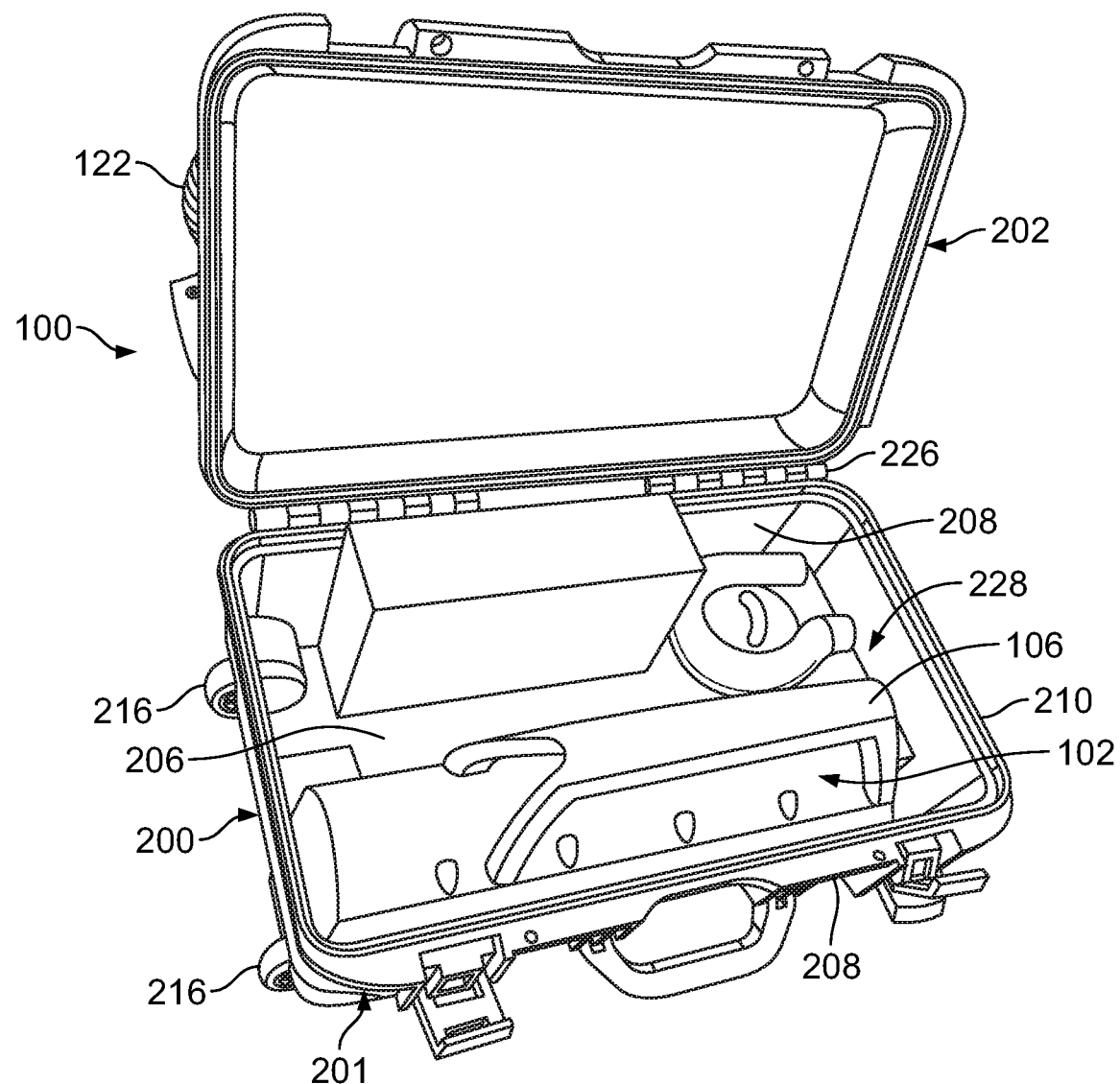
FIG. 20 illustrates a perspective view of the portable sanitizing system having a case assembly in an open position, according to an embodiment of the present disclosure.

FIG. 20 illustrates a perspective view of the portable sanitizing system 100 having the case assembly 200 in an open position, according to an embodiment of the present disclosure. As shown, the cover 202 is opened via a hinge 226 that pivotally couples the cover 202 to the main body 201.

An internal or storage chamber 228 is defined between the base 204, the lateral walls 208, the rear wall 206, and the top wall 210 (and the cover 202, when closed). Various components of the portable sanitizing system 100 may be stored within the storage chamber 228. For example, the components within the backpack assembly 104, as described with respect to FIG. 16, may be contained within the storage chamber 228.

For example, when not in use, the wand assembly 102 is contained within the storage chamber 228. Additionally, one or more batteries, such as rechargeable Lithium batteries, may be contained within the storage chamber 228.

An air generation sub-system (such as a cooling fan) may also be contained within the storage chamber 228. The air generation sub-system may be in fluid communication with an air tube within the hose 122. The hose 122 may be removably connected to the air generation sub-system. In at least one embodiment, the hose 122 is configured to be coupled to and uncoupled from the wand assembly 102 and the air generation sub-system. That is, the hose 122 may be removably coupled to the wand assembly 102 and the air generation sub-system.

One or more air filters, such as carbon filters, may also be within the storage chamber 228. The air filters may be in communication with the air tube or other such delivery duct or line that routes air through the hose 122.

Figures 21, 22:
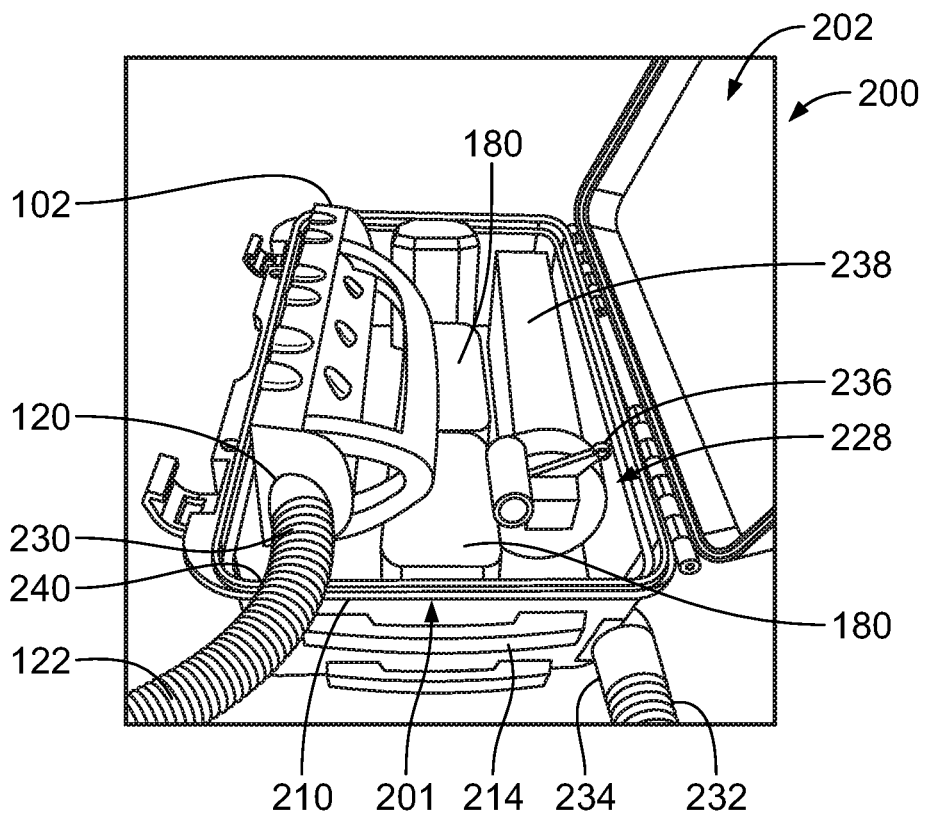
FIG. 21 illustrates a perspective view of the portable sanitizing system having the case assembly in the open position, according to an embodiment of the present disclosure.
FIG. 22 illustrates a perspective view of the portable sanitizing system having the case assembly in the open position, according to an embodiment of the present disclosure.

FIG. 21 illustrates a perspective view of the portable sanitizing system 100 having the case assembly 200 in the open position, according to an embodiment of the present disclosure. The wand assembly 102 is configured to be stowed in the storage chamber 228. When the wand assembly 102 is to be used, the cover 202 is opened, and a first end 230 of the hose 122 is coupled to the port 120 of the wand assembly 102. In at least one embodiment, the hose 122 is configured to channel cooling air into the wand assembly 102, in order to cool the UV lamp 140 during activation.

A second end 232 of the hose 122 may be connected to a port 234 extending into and through a portion of the main body 201, such as through a portion of the top wall 210. The port 234 connects the hose 122 to an air generation sub-system, such as a cooling fan 236 that is within the storage chamber 228. The cooling fan 236 may be activated to generate cooling air that is delivered to the wand assembly 102 through the hose 122 (such as an air tube within the hose 122, or through an internal passage of the hose 122 itself).

One or more batteries 180 may also be stowed within the storage chamber 228. For example, three batteries 180 may be within the storage chamber 228.

A power supply 238 is also contained within the storage chamber 228. The power supply 238 may be coupled to the wand assembly 102 through a power cord (such as via a plug and receptacle fitting) to provide power to the wand assembly 102. Further, the power supply 238 may be configured to provide power to the batteries 180 (such as to recharge the batteries 180). The batteries 180 may be secured to the wand assembly 102 and provide power to the wand assembly 102, so that the wand assembly 102 may be used without connection to the power supply 238.

The cooling fan 236 couples to the hose 122 via the port 234. The cooling fan 236 may also include a diverter port 237 that couples to an internal portion of the power supply 238. In this manner, cooling air may be delivered to both the hose 122 (and therefore the wand assembly 102), and the power supply 238, thereby providing cooling to both the wand assembly 102 and the power supply 238.

A hole 240 may be formed through a portion of the case assembly 200. For example, a hole 240 may be formed through a portion of the top wall 210 and sized and shaped to allow the hose 122 to pass therethrough. In this manner, the hose 122 may remain connected to the wand assembly 102 even when the wand assembly 102 is contained within the storage chamber 228 and the cover 202 is closed. Other portions of the hose 122 between the first end 230 and the second end 232 may be secured to the cover 202 by the hose retainer 218, as shown and described with respect to FIG. 19.

As shown, the handle 214 may be secured to the top wall 210 of the main body 201. The handle 214 may be configured to retracted into and extend out of the main body 201. For example, the handle 214 may be a telescoping handle.

The wand assembly 102 is removably secured within the storage chamber 228. For example, the wand assembly 102 may be removably secured within the storage chamber 228 by one or more latches, clips, or via an interference fir with a conforming portion of the case assembly 200.

The power supply 238 may be fixed in position within the storage chamber 228. For example, the power supply 238 may be fixed in the storage chamber 228 by one or more fasteners, adhesives, or the like. Optionally, the power supply 238 may be secured in position by one or more latches, clips, or the like.

The batteries 180 may similarly be fixed position within the storage chamber 228. For example, the batteries 180 may be fixed in the storage chamber 228 by one or more fasteners, adhesives, or the like. Optionally, the batteries 180 may be secured in position by one or more latches, clips, or the like. In at least one other embodiment, the batteries 180 may be removable, and configured to couple directly to the wand assembly 102 to provide power thereto.

FIG. 22 illustrates a perspective view of the portable sanitizing system 100 having the case assembly 200 in the open position, according to an embodiment of the present disclosure. A power cord 250 may also be stowed within the storage chamber 228. The power cord 250 is contained within the case assembly 200 when the cover 202 is closed and the portable sanitizing system 100 is moved when the wand assembly 102 is not being operated.

Optionally, the power cord 250 connects the power supply 238 to a source of power (such as a wall outlet). In addition to supply air to the wand assembly 102, the hose 122 also routes electrical cables and the like to the wand assembly 102 from the power supply 238 and the batteries 180.

Optionally, the hose 122 may not include electrical connections to the wand assembly 102. Instead, the wand assembly 102, the power cord 250 may plug into the wand assembly 102, via the plug 252, to supply power from the power supply 238 and/or the batteries 180. In this embodiment, as the wand assembly 102 is operated, the plug 252 of the power cord 250 is connected to a reciprocal receptacle of the wand assembly 102. An opposite end of the power cord 250 is connected to the power supply 238 (and/or, a battery 180). The power cord 250 extends out of the case assembly 200 through the hole 240. Thus, the wand assembly 102 may be removed from the storage chamber 228 and connected to the hose 122 and the power cord 250, which extend through the hole 240. The cover 202 may then be closed, thereby securely retaining the power supply 238, the batteries 180, and the like within the storage chamber 228. The wand assembly 102 may then be activated, as it is powered via the power supply 238 or one or more of the batteries 180, and the closed case assembly 200 may be moved, such as via an individual grasping the handle 214 and rolling the case assembly 200 via the casters 216 (shown in FIGS. 19 and 20).

Further, the hole 240 also allows intake air to be drawn into the storage chamber 228, even when the cover 202 is closed over the main body 201. Accordingly, the cooling fan 236 is able to receive fresh air, even when the cover 202 is closed.

The power supply 238 may be configured to receive power from a standard power supply, such as a source of alternating current power. For example, the power supply 238 may connect to the source of alternating current power through a power cord. The power cord 250 connects to the wand assembly 252, and is configured to deliver power to the wand assembly 102 to operate the UV lamp 140 from power received from the power supply 238 and optionally the batteries 180. For example, when the power supply 238 is connected to a source of alternating current power, the wand assembly 102 is powered by the power supply 238. In the absence of such power, the wand assembly 102 may be powered by the batteries 180. For example, the wand assembly 102 receives power from the batteries 180 the power supply 238 is not plugged into a power outlet. If the power supply 238 is plugged into a power outlet, one or more relays in the power supply 238 switch over from the batteries 180 to alternating current power supply from the power outlet.

Figure 23:
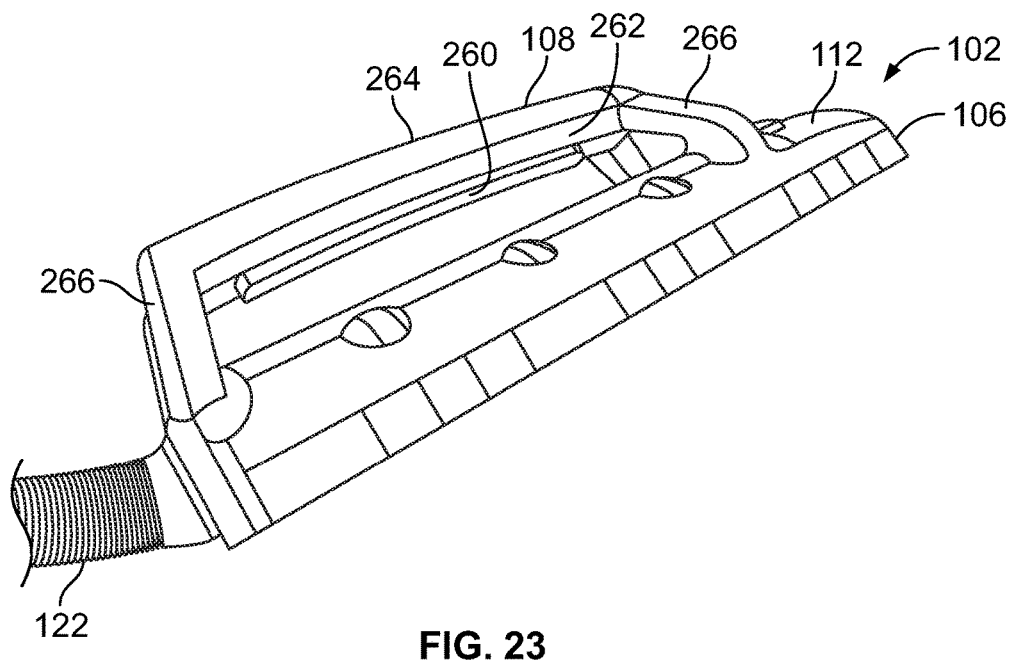
FIG. 23 illustrates a perspective lateral view of the wand assembly, according to an embodiment of the present disclosure.

FIG. 23 illustrates a perspective lateral view of the wand assembly 102, according to an embodiment of the present disclosure. As shown, the handle 108 may be fixed in relation to the shroud 112. For example, the handle 108 may be integrally molded and formed with the shroud 112. The wand assembly 102 may be small and compact in order to fit in confined spaced, such as within a flight deck of an aircraft.

An activation trigger 260 is moveably coupled to the handle 108. For example, the activation trigger 260 may be secured to an underside 262 of a main beam 264 of the handle 108. The activation trigger 260 is configured to be selectively pressed and/or depressed to activate and deactivate the UV lamp 140 of the wand assembly 102, as desired.

The activation trigger 260 may be located anywhere along the length of the handle 108. The activation trigger 260 may be shaped differently than shown. Further, the activation trigger 260 may be smaller or larger than shown. As an example, the activation trigger 260 may be a circular button, instead of an elongated bar or beam, as shown. Also, optionally, the activation trigger 260 may be located on a top portion of the main beam 264, or on an extension beam 266, which spaces the handle 108 from the shroud 112. As another example, the activation trigger 260 may be located on a portion of the shroud 112.

Figure 24:
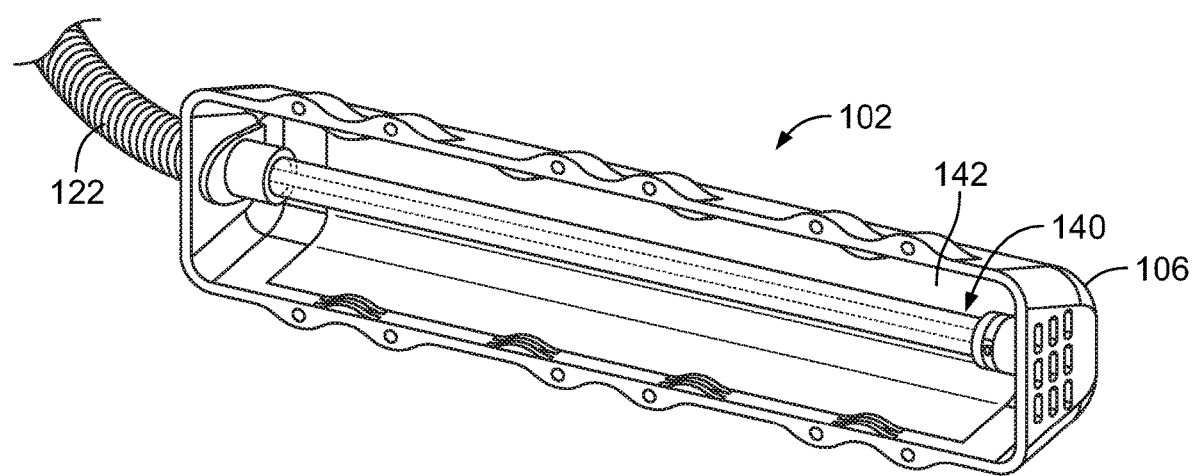
FIG. 24 illustrates a perspective bottom view of the wand assembly of FIG. 23.

FIG. 24 illustrates a perspective bottom view of the wand assembly 102 of FIG. 23. As shown, the reflector 142 is secured to an underside of the shroud 112.

Figure 25:
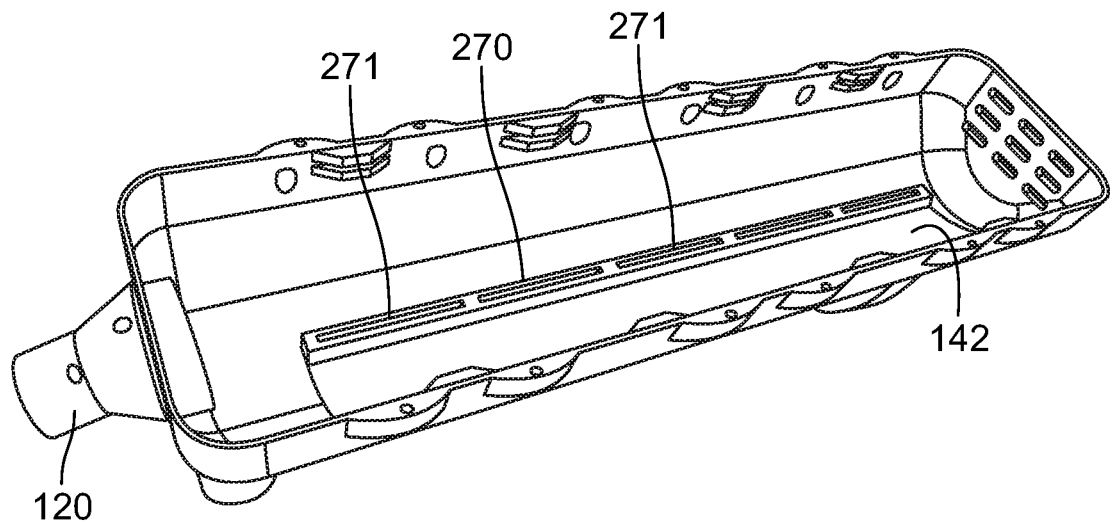
FIG. 25 illustrates a perspective bottom view of the wand assembly of FIGS. 23 and 24 without the UV lamp, according to an embodiment of the present disclosure.
Figure 26:
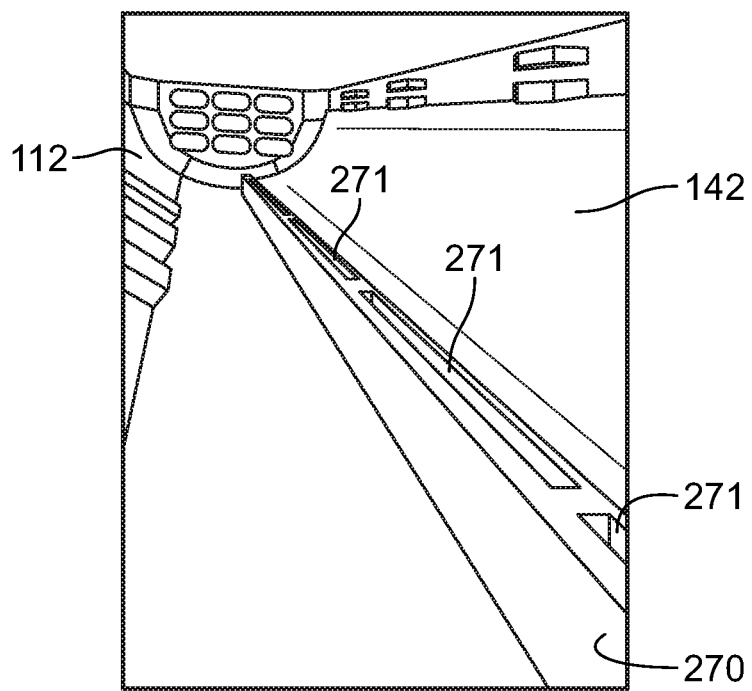
FIG. 26 illustrates a perspective view of a cooling manifold of a shroud of the wand assembly, according to an embodiment of the present disclosure.

FIG. 25 illustrates a perspective bottom view of the wand assembly 102 of FIGS. 23 and 24 without the UV lamp 140 (for the sake of clarity), according to an embodiment of the present disclosure. FIG. 26 illustrates a perspective view of a cooling manifold 270 of the shroud 112 of the wand assembly 102. Referring to FIGS. 25 and 26, a half of the reflector 142 is removed to expose a cooling manifold 270 that extends through the shroud 112 and is in fluid communication with the port 120. The cooling manifold 270 has a plurality of air outlets 271 that allow air delivered through the hose 122 (shown in FIG. 23, for example) that is coupled to the port 120 to pass over the UV lamp 140 when activated. In this manner, the UV lamp 140 is cooled during operation. The delivered air passes over and around the reflector 142 (which is disposed between the cooling manifold 270 and the UV lamp 140), through a channel defined through the reflector 142, and/or between two portions of the reflector 142 (such as a first half of the reflector 142 and a second half of the reflector 142).

Referring to FIGS. 19-26, the portable sanitizing system 100 includes the wand assembly 102 including the sanitizing head 106 having the UV lamp 140. The case assembly 200 includes the cover 202 coupled to the main body 201. The cover 202 is configured to be moved between an open position that exposes the storage chamber 228 and a closed position. The wand assembly 102 is configured to be stored in the storage chamber 228 when not in use and removed from the storage chamber 228 to disinfect one or more components with UV light emitted by the UV lamp 140.

In at least one embodiment, the portable sanitizing system 100 includes the wand assembly 102 and the case assembly 200, which may be a rolling case assembly. The wand assembly 102 includes the UV lamp 140. The cooling manifold 270 is configured to allow air to blow across the UV lamp 140, such as one or more bulbs of the UV lamp 140. The wand assembly 102 may also include a two piece reflector 142, a master power switch, and a trigger switch, such as the activation trigger 260, to activate and illuminate the UV lamp 140.

During use of the wand assembly 102, the case assembly 200 may be placed away from the area being disinfected, thereby allowing the operator to transport only the wand assembly 102 to the area, and facilitating movement and operation in tight or confined spaces. The wand assembly 102 may include a 300 watt, 222 nm UV lamp, optional ranging lights, the cooling manifold 270 running the length of the shroud 112, the reflector 142, mounts (such as brackets, clamps, fasteners, and/or the like) to secure the UV lamp 140 to the shroud 112, a master power switch on the handle 108, and the activation trigger 260 on the handle 108 that is configured to be engaged to selectively activate and deactivate the UV lamp 140. The reflector 142 may be made out of Teflon or an aluminum sheet, which allows the reflector 142 to provide electromagnetic shielding. The UV lamp 140 may be attached to the shroud 112 with wire straps or bands, which may be positioned on top of Teflon tape and dry woven fiberglass that serve as a cushion between the strap and the glass bulb.

Figure 27:
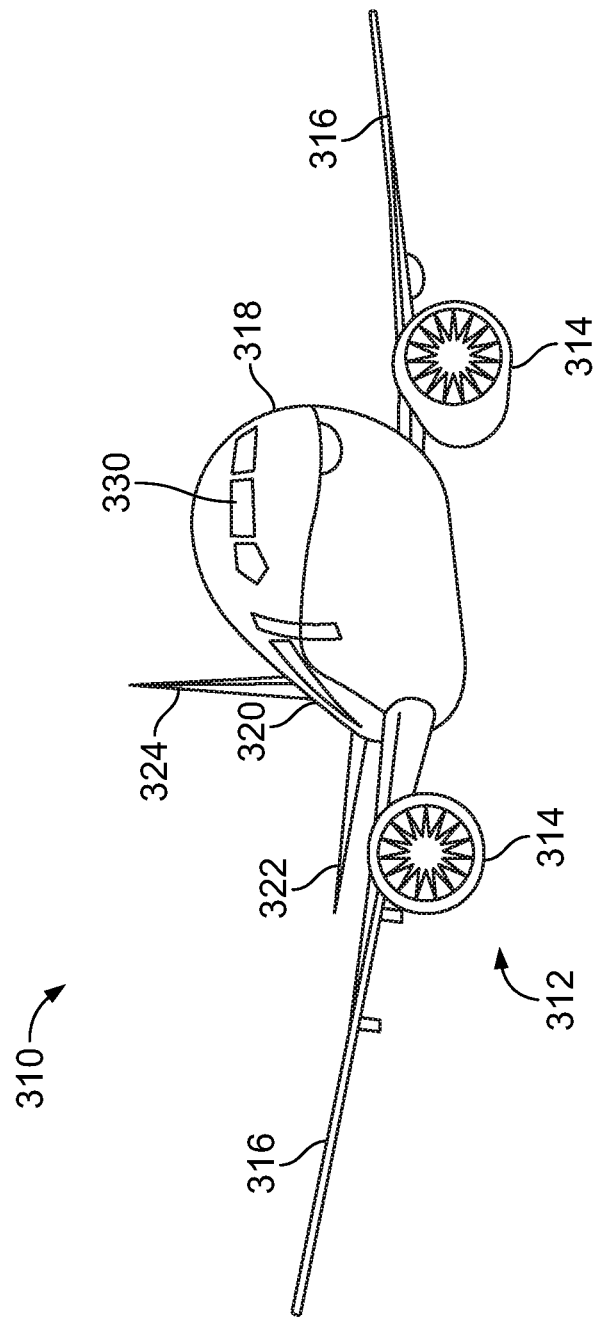
FIG. 27 illustrates a perspective front view of an aircraft, according to an embodiment of the present disclosure.

FIG. 27 illustrates a perspective front view of an aircraft 310, according to an embodiment of the present disclosure. The aircraft 310 includes a propulsion system 312 that includes engines 314, for example. Optionally, the propulsion system 312 may include more engines 314 than shown. The engines 314 are carried by wings 316 of the aircraft 310. In other embodiments, the engines 314 may be carried by a fuselage 318 and/or an empennage 320. The empennage 320 may also support horizontal stabilizers 322 and a vertical stabilizer 324.

The fuselage 318 of the aircraft 310 defines an internal cabin 330, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 330 includes one or more lavatory systems, lavatory units, or lavatories, as described herein.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 28A:
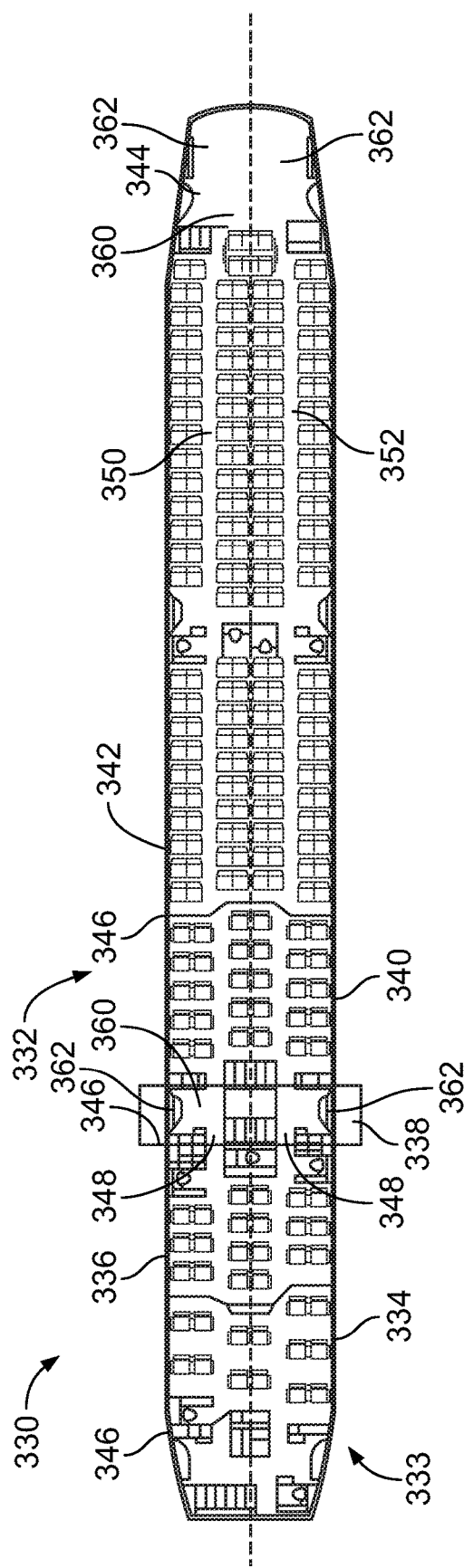
FIG. 28A illustrates a top plan view of an internal cabin of an aircraft, according to an embodiment of the present disclosure.

FIG. 28A illustrates a top plan view of an internal cabin 330 of an aircraft, according to an embodiment of the present disclosure. The internal cabin 330 may be within the fuselage 332 of the aircraft, such as the fuselage 318 of FIG. 27. For example, one or more fuselage walls may define the internal cabin 330. The internal cabin 330 includes multiple sections, including a front section 333, a first class section 334, a business class section 336, a front galley station 338, an expanded economy or coach section 340, a standard economy of coach section 342, and an aft section 344, which may include multiple lavatories and galley stations. It is to be understood that the internal cabin 330 may include more or less sections than shown. For example, the internal cabin 330 may not include a first class section, and may include more or less galley stations than shown. Each of the sections may be separated by a cabin transition area 346, which may include class divider assemblies between aisles 348.

As shown in FIG. 28A, the internal cabin 330 includes two aisles 350 and 352 that lead to the aft section 344. Optionally, the internal cabin 330 may have less or more aisles than shown. For example, the internal cabin 330 may include a single aisle that extends through the center of the internal cabin 330 that leads to the aft section 344.

The aisles 348, 350, and 352 extend to egress paths or door passageways 360. Exit doors 362 are located at ends of the egress paths 360. The egress paths 360 may be perpendicular to the aisles 348, 350, and 352. The internal cabin 330 may include more egress paths 360 at different locations than shown. The portable sanitizing system 100 shown and described with respect to FIGS. 1-26 may be used to sanitize various structures within the internal cabin 330, such as passenger seats, monuments, stowage bin assemblies, components on and within lavatories, galley equipment and components, and/or the like.

Figure 28B:
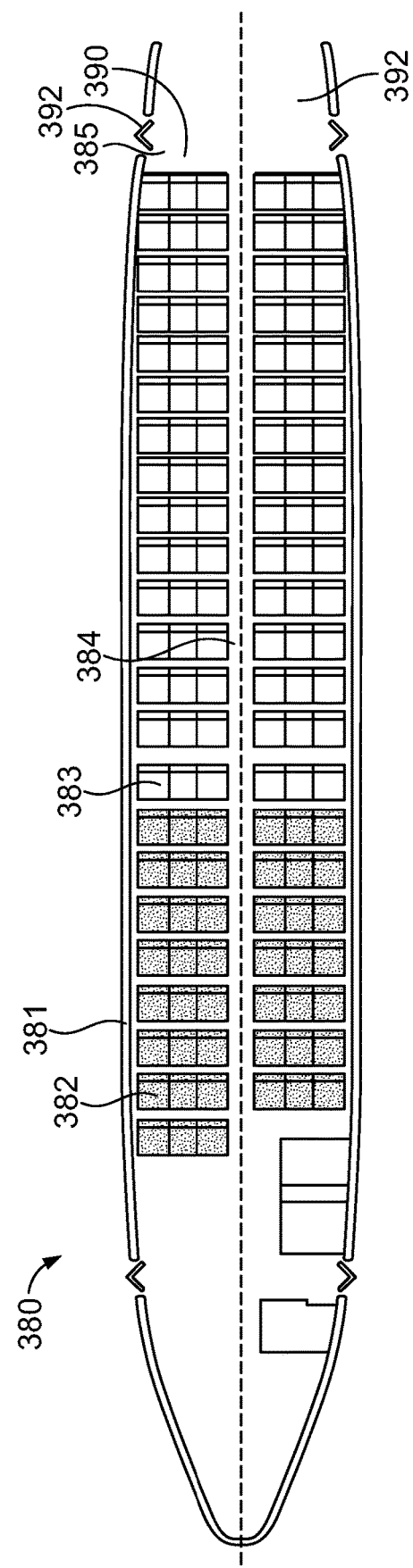
FIG. 28B illustrates a top plan view of an internal cabin of an aircraft, according to an embodiment of the present disclosure.

FIG. 28B illustrates a top plan view of an internal cabin 380 of an aircraft, according to an embodiment of the present disclosure. The internal cabin 380 is an example of the internal cabin 330 shown in FIG. 27. The internal cabin 380 may be within a fuselage 381 of the aircraft. For example, one or more fuselage walls may define the internal cabin 380. The internal cabin 380 includes multiple sections, including a main cabin 382 having passenger seats 383, and an aft section 385 behind the main cabin 382. It is to be understood that the internal cabin 380 may include more or less sections than shown.

The internal cabin 380 may include a single aisle 384 that leads to the aft section 385. The single aisle 384 may extend through the center of the internal cabin 380 that leads to the aft section 385. For example, the single aisle 384 may be coaxially aligned with a central longitudinal plane of the internal cabin 380.

The aisle 384 extends to an egress path or door passageway 390. Exit doors 392 are located at ends of the egress path 390. The egress path 390 may be perpendicular to the aisle 384. The internal cabin 380 may include more egress paths than shown. The portable sanitizing system 100 shown and described with respect to FIGS. 1-26 may be used to sanitize various structures within the internal cabin 330, such as passenger seats, monuments, stowage bin assemblies, components on and within lavatories, galley equipment and components, and/or the like.

Figure 29:
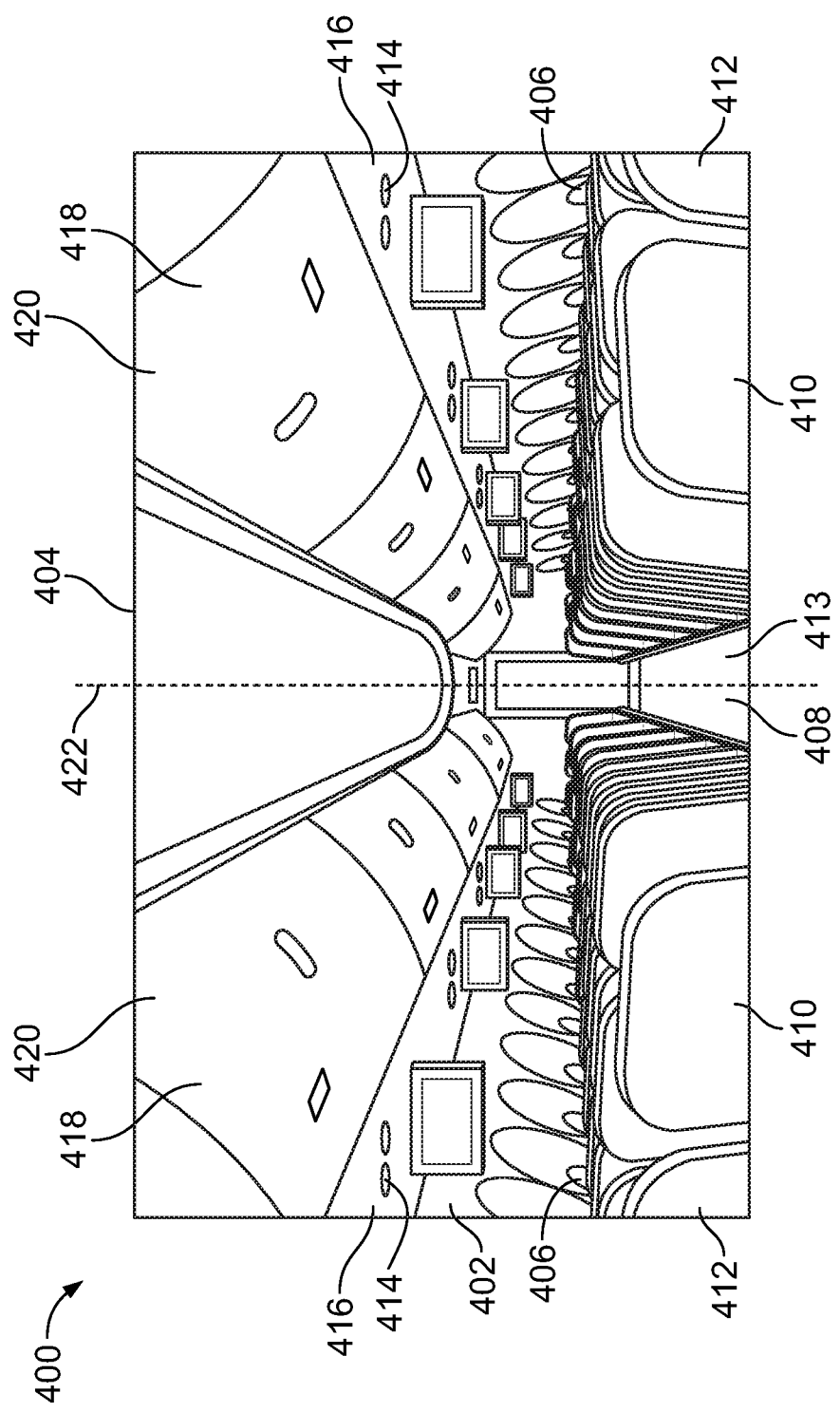
FIG. 29 illustrates a perspective interior view of an internal cabin of an aircraft, according to an embodiment of the present disclosure.

FIG. 29 illustrates a perspective interior view of an internal cabin 400 of an aircraft, according to an embodiment of the present disclosure. The internal cabin 400 includes outboard walls 402 connected to a ceiling 404. Windows 406 may be formed within the outboard walls 402. A floor 408 supports rows of seats 410. As shown in FIG. 29, a row 412 may include two seats 410 on either side of an aisle 413. However, the row 412 may include more or less seats 410 than shown. Additionally, the internal cabin 400 may include more aisles than shown.

Passenger service units (PSUs) 414 are secured between an outboard wall 402 and the ceiling 404 on either side of the aisle 413. The PSUs 414 extend between a front end and rear end of the internal cabin 400. For example, a PSU 414 may be positioned over each seat 410 within a row 412. Each PSU 414 may include a housing 416 that generally contains vents, reading lights, an oxygen bag drop panel, an attendant request button, and other such controls over each seat 410 (or groups of seats) within a row 412.

Overhead stowage bin assemblies 418 are secured to the ceiling 404 and/or the outboard wall 402 above and inboard from the PSU 414 on either side of the aisle 413. The overhead stowage bin assemblies 418 are secured over the seats 410. The overhead stowage bin assemblies 418 extend between the front and rear end of the internal cabin 400. Each stowage bin assembly 418 may include a pivot bin or bucket 420 pivotally secured to a strongback (hidden from view in FIG. 29). The overhead stowage bin assemblies 418 may be positioned above and inboard from lower surfaces of the PSUs 414. The overhead stowage bin assemblies 418 are configured to be pivoted open in order to receive passenger carry-on baggage and personal items, for example.

As used herein, the term "outboard" means a position that is further away from a central longitudinal plane 422 of the internal cabin 400 as compared to another component. The term "inboard" means a position that is closer to the central longitudinal plane 422 of the internal cabin 400 as compared to another component. For example, a lower surface of a PSU 414 may be outboard in relation to a stowage bin assembly 418.

The portable sanitizing system 100 shown and described with respect to FIGS. 1-26 may be used to sanitize various structures shown within the internal cabin 400.

When not in use, the portable sanitizing system 100 may be stored within a closet, galley cart bay, or galley cart, such as within the internal cabin of the vehicle.

Figure 30:
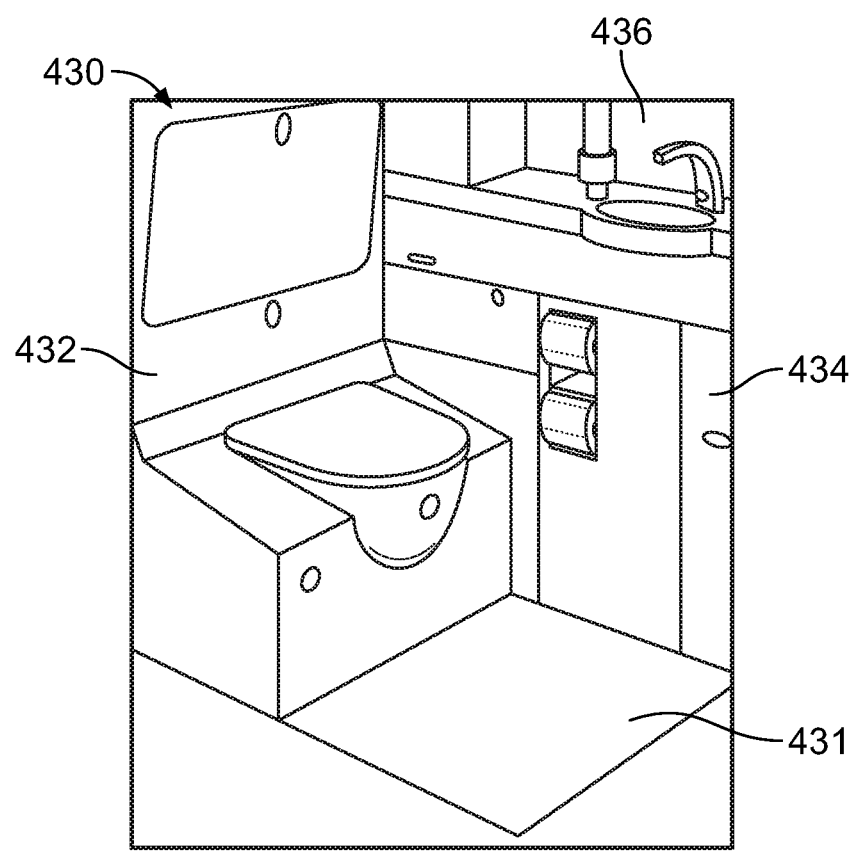
FIG. 30 illustrates a perspective internal view of a lavatory within an internal cabin of an aircraft.

FIG. 30 illustrates a perspective internal view of a lavatory 430 within an internal cabin of a vehicle, such as any of the internal cabins described herein. The lavatory 430 is an example of an enclosed space, monument or chamber, such as within the internal cabin a vehicle. The lavatory 430 may be onboard an aircraft, as described above. Optionally, the lavatory 430 may be onboard various other vehicles. In other embodiments, the lavatory 430 may be within a fixed structure, such as a commercial or residential building. The lavatory 430 includes a base floor 431 that supports a toilet 432, cabinets 434, and a sink 436 or wash basin. The lavatory 430 may be arranged differently than shown. The lavatory 430 may include more or less components than shown. The portable sanitizing system 100 shown and described with respect to FIGS. 1-26 may be used to sanitize the various structures, components, and surfaces within the lavatory 430.

The portable sanitizing systems 100 as described herein can be used to safely and effectively sanitize high-touch surfaces in the flight deck and internal cabin in a timely and cost-effective manner. UV disinfection allows the internal cabin to be quickly and effectively disinfected, such as between flights. In at least one embodiment, the portable sanitizing system 100 is used to augment a cleaning process, such as after manual cleaning.

Figure 31:
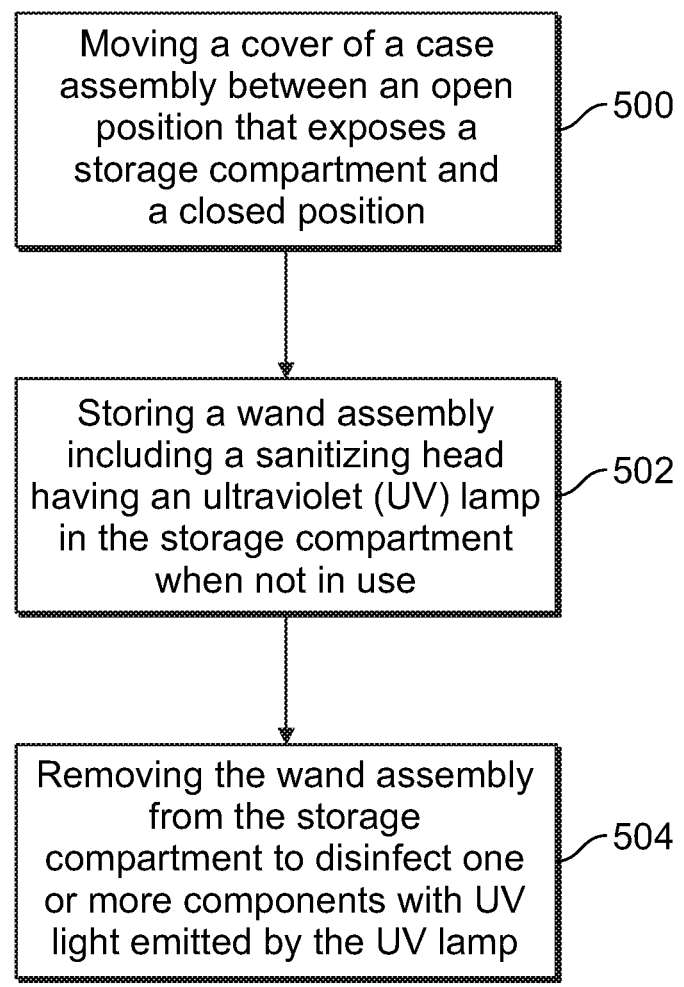
FIG. 31 illustrates a flow chart of a portable sanitizing method, according to an embodiment of the present disclosure.

FIG. 31 illustrates a flow chart of a portable sanitizing method, according to an embodiment of the present disclosure. The portable sanitizing method includes moving, at 500, a cover of a case assembly between an open position that exposes a storage chamber and a closed position; storing, at 502, a wand assembly including a sanitizing head having an ultraviolet (UV) lamp in the storage chamber when not in use; and removing, at 504, the wand assembly from the storage chamber to disinfect one or more components with UV light emitted by the UV lamp.

In at least one embodiment, the portable sanitizing method also includes rolling the case assembly with one or more casters.

In at least one embodiment, the portable sanitizing method also includes securing a hose on the cover with a hose retainer when the wand assembly is within the storage chamber and the cover is the closed position.

In at least one embodiment, the portable sanitizing method also includes disposing a cooling fan within the storage chamber; coupling the cooling fan to the wand assembly through a hose; and delivering, by the cooling fan, cooling air to the wand assembly through the hose.

The portable sanitizing method may also include disposing one or more batteries within the storage chamber. The portable sanitizing method may also include disposing a power supply within the storage chamber; and coupling the power supply is configured to the wand assembly through a power cord.

The portable sanitizing method may also include allowing one or both of a portion of a hose or a portion of a power cord to pass through a hole formed through a portion of the case assembly.

In at least one embodiment, the portable sanitizing method also includes delivering, by a cooling manifold of the wand assembly, cooling air to the UV lamp.

Further, the disclosure comprises embodiments according to the following clauses:

Clause 1. A portable sanitizing system, comprising:
a wand assembly including a sanitizing head having an ultraviolet (UV) lamp; and
a case assembly including a cover coupled to a main body, wherein the cover is configured to be moved between an open position that exposes a storage chamber and a closed position, wherein the wand assembly is configured to be stored in the storage chamber when not in use and removed from the storage chamber to disinfect one or more components with UV light emitted by the UV lamp.

Clause 2. The portable sanitizing system of Clause 1, wherein the UV lamp is configured to emit the UV light having a wavelength between 200 nm-230 nm to disinfect a surface.

Clause 3. The portable sanitizing system of Clause 1, wherein the UV lamp is configured to emit the UV light having a wavelength of 222 nm to disinfect a surface.

Clause 4. The portable sanitizing system of Clause 1, wherein the UV lamp is configured to emit the UV light having a wavelength between 230 nm-280 nm to disinfect a surface.

Clause 5. The portable sanitizing system of Clause 1, wherein the UV lamp is configured to emit the UV light having a wavelength of 254 nm to disinfect a surface.

Clause 6. The portable sanitizing system of any of Clauses 1-5, wherein the case assembly comprises a handle.

Clause 7. The portable sanitizing system of any of Clauses 1-6, wherein the case assembly further comprises a hose retainer that is configured to secure a hose on the cover when the wand assembly is within the storage chamber and the cover is the closed position.

Clause 8. The portable sanitizing system of Clause 7, wherein the hose retainer comprises a flexible fabric sheet.

Clause 9. The portable sanitizing system of any of Clauses 1-8, further comprising a cooling fan within the storage chamber, wherein the cooling fan is configured to couple to the wand assembly through a hose, and wherein the cooling fan is configured to deliver cooling air to the wand assembly through the hose.

Clause 10. The portable sanitizing system of any of Clauses 1-9, further comprising one or more batteries within the storage chamber.

Clause 11. The portable sanitizing system of any of Clauses 1-10, further comprising a power supply within the storage chamber, wherein the power supply is configured to couple to the wand assembly through a power cord.

Clause 12. The portable sanitizing system of any of Clauses 1-11, wherein a hole is formed through a portion of the case assembly, wherein the hole is configured to allow one or both of a portion of a hose or a portion of a power cord to pass.

Clause 13. The portable sanitizing system of any of Clauses 1-12, wherein the wand assembly comprises an activation trigger secured to an underside of a main beam of a handle.

Clause 14. The portable sanitizing system of any of Clauses 1-13, wherein the wand assembly further comprises a cooling manifold that is configured to deliver cooling air to the UV lamp.

Clause 15. A portable sanitizing method, comprising:

moving a cover of a case assembly between an open position that exposes a storage chamber and a closed position;

storing a wand assembly including a sanitizing head having an ultraviolet (UV) lamp in the storage chamber when not in use; and removing the wand assembly from the storage chamber to disinfect one or more components with UV light emitted by the UV lamp.

Clause 16. The portable sanitizing method of Clause 15, further comprising securing a hose on the cover with a hose retainer when the wand assembly is within the storage chamber and the cover is the closed position.

Clause 17. The portable sanitizing method of Clauses 15 or 16, further comprising:

disposing a cooling fan within the storage chamber;

coupling the cooling fan to the wand assembly through a hose; and delivering, by the cooling fan, cooling air to the wand assembly through the hose.

Clause 18. The portable sanitizing method of any of Clauses 15-17, further comprising disposing one or more batteries within the storage chamber.

Clause 19. The portable sanitizing method of any of Clauses 15-18, further comprising:

disposing a power supply within the storage chamber; and coupling the power supply to the wand assembly through a power cord.

Clause 20. The portable sanitizing method of any of Clauses 15-19, further comprising allowing one or both of a portion of a hose or a portion of a power cord to pass through a hole formed through a portion of the case assembly.

Clause 21. The portable sanitizing method of any of Clauses 15-20, further comprising delivering, by a cooling manifold of the wand assembly, cooling air to the UV lamp.

Clause 22. A portable sanitizing system, comprising:

a wand assembly including a sanitizing head having an ultraviolet (UV) lamp, and a cooling manifold that is configured to deliver cooling air to the UV lamp; and a case assembly comprising:

a handle;

a cover coupled to a main body, wherein the cover is configured to be moved between an open position that exposes a storage chamber and a closed position, wherein the wand assembly is configured to be stored in the storage chamber when not in use and removed from the storage chamber to disinfect one or more components with UV light emitted by the UV lamp;

one or more casters;

a hose retainer that is configured to secure a hose on the cover when the wand assembly is within the storage chamber and the cover is the closed position;

a cooling fan within the storage chamber, wherein the cooling fan is configured to couple to the wand assembly through the hose, and wherein the cooling fan is configured to deliver cooling air to the wand assembly through the hose;

one or more batteries within the storage chamber;

a power supply within the storage chamber, wherein the power supply is configured to couple to the wand assembly through a power cord, wherein a hole is formed through a portion of the case assembly, wherein the hole is configured to allow one or both of a portion of a hose or a portion of a power cord to pass.

As described herein, embodiments of the present disclosure provide systems and a methods for efficiently sterilizing surfaces, components, structures, and/or the like within an internal cabin of a vehicle. Further, embodiments of the present disclosure provide compact, easy-to-use, and safe systems and methods for using UV light to sterilize surfaces within an internal cabin.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A portable sanitizing system, comprising:
   a wand assembly including a sanitizing head having an ultraviolet (UV) lamp; and
   a case assembly including:
      a cover coupled to a main body, wherein the cover is configured to be moved between an open position that exposes a storage chamber, and a closed position, wherein the wand assembly is configured to be stored in the storage chamber when not in use and removed from the storage chamber to disinfect one or more components with UV light emitted by the UV lamp; and
      a hose retainer that is configured to secure a hose on the cover when the wand assembly is within the storage chamber and the cover is in the closed position.

2. The portable sanitizing system of claim 1, wherein the UV lamp is configured to emit the UV light having a wavelength between 200 nm-230 nm to disinfect a surface.

3. The portable sanitizing system of claim 1, wherein the UV lamp is configured to emit the UV light having a wavelength of 222 nm to disinfect a surface.

4. The portable sanitizing system of claim 1, wherein the UV lamp is configured to emit the UV light having a wavelength between 230 nm-280 nm to disinfect a surface.

5. The portable sanitizing system of claim 1, wherein the UV lamp is configured to emit the UV light having a wavelength of 254 nm to disinfect a surface.

6. The portable sanitizing system of claim 1, wherein the case assembly further comprises a handle.

7. The portable sanitizing system of claim 1, wherein the hose retainer comprises a flexible fabric sheet.

8. The portable sanitizing system of claim 1, wherein the case assembly further comprises a cooling fan within the storage chamber, wherein the cooling fan is configured to couple to the wand assembly through the hose, and wherein the cooling fan is configured to one or both of deliver cooling air to, or draw the cooling air into the wand assembly through the hose.

9. The portable sanitizing system of claim 1, wherein the case assembly further comprises one or more batteries within the storage chamber.

10. The portable sanitizing system of claim 1, wherein the case assembly further comprises a power supply within the storage chamber, wherein the power supply is configured to couple to the wand assembly through a power cord.

11. The portable sanitizing system of claim 1, wherein a hole is formed through a portion of the case assembly, wherein the hole is configured to allow one or both of a portion of a hose or a portion of a power cord to pass.

12. The portable sanitizing system of claim 1, wherein the wand assembly further comprises an activation trigger secured to an underside of a main beam of a handle.

13. The portable sanitizing system of claim 1, wherein the wand assembly further comprises a cooling manifold that is configured to deliver cooling air to the UV lamp.

14. A portable sanitizing system, comprising:
    a wand assembly including a sanitizing head having an ultraviolet (UV) lamp, and a cooling manifold that is configured to deliver cooling air to the UV lamp; and
    a case assembly comprising:
       a handle;
       a cover coupled to a main body, wherein the cover is configured to be moved between an open position that exposes a storage chamber, and a closed position, wherein the wand assembly is configured to be stored in the storage chamber when not in use and removed from the storage chamber to disinfect one or more components with UV light emitted by the UV lamp;
       one or more casters;
       a hose retainer that is configured to secure a hose on the cover when the wand assembly is within the storage chamber and the cover is in the closed position;
       a cooling fan within the storage chamber, wherein the cooling fan is configured to couple to the wand assembly through the hose, and wherein the cooling fan is configured to deliver cooling air to the wand assembly through the hose;
       one or more batteries within the storage chamber; and
       a power supply within the storage chamber, wherein the power supply is configured to couple to the wand assembly through a power cord, wherein a hole is formed through a portion of the case assembly, wherein the hole is configured to allow one or both of a portion of a hose or a portion of a power cord to pass.

15. A portable sanitizing system, comprising:
    a wand assembly including a sanitizing head having an ultraviolet (UV) lamp; and
    a case assembly including:
       a cover coupled to a main body, wherein the cover is configured to be moved between an open position that exposes a storage chamber, and a closed position, wherein the wand assembly is configured to be stored in the storage chamber when not in use and removed from the storage chamber to disinfect one or more components with UV light emitted by the UV lamp; and
       a cooling fan within the storage chamber, wherein the cooling fan is configured to couple to the wand assembly through a hose, and wherein the cooling fan is configured to one or both of deliver cooling air to, or draw the cooling air into the wand assembly through the hose.

16. The portable sanitizing system of claim 15, wherein the UV lamp is configured to emit the UV light having a wavelength between 200 nm-230 nm to disinfect a surface.

17. The portable sanitizing system of claim 15, wherein the UV lamp is configured to emit the UV light having a wavelength of 222 nm to disinfect a surface.

18. The portable sanitizing system of claim 15, wherein the UV lamp is configured to emit the UV light having a wavelength between 230 nm-280 nm to disinfect a surface.

19. The portable sanitizing system of claim 15, wherein the UV lamp is configured to emit the UV light having a wavelength of 254 nm to disinfect a surface.

20. The portable sanitizing system of claim 15, wherein the case assembly further comprises a handle.

21. The portable sanitizing system of claim 15, wherein the case assembly further comprises one or more batteries within the storage chamber.

22. The portable sanitizing system of claim 15, wherein the case assembly further comprises a power supply within the storage chamber, wherein the power supply is configured to couple to the wand assembly through a power cord.

23. The portable sanitizing system of claim 15, wherein a hole is formed through a portion of the case assembly, wherein the hole is configured to allow one or both of a portion of a hose or a portion of a power cord to pass.

24. The portable sanitizing system of claim 15, wherein the wand assembly further comprises an activation trigger secured to an underside of a main beam of a handle.

25. The portable sanitizing system of claim 15, wherein the wand assembly further comprises a cooling manifold that is configured to deliver cooling air to the UV lamp.

26. A portable sanitizing system, comprising:
a wand assembly including:
a sanitizing head having an ultraviolet (UV) lamp; and
a cooling manifold that is configured to deliver cooling air to the UV lamp; and
a case assembly including:
a cover coupled to a main body, wherein the cover is configured to be moved between an open position that exposes a storage chamber and a closed position, wherein the wand assembly is configured to be stored in the storage chamber when not in use and removed from the storage chamber to disinfect one or more components with UV light emitted by the UV lamp; and one or more of:
a cooling fan within the storage chamber, wherein the cooling fan is configured to couple to the wand assembly through a hose, and wherein the cooling fan is configured to one or both of deliver the cooling air to, or draw the cooling air into the wand assembly through the hose;
one or more batteries within the storage chamber; or
a power supply within the storage chamber, wherein the power supply is configured to couple to the wand assembly through a power cord.

27. The portable sanitizing system of claim 26, wherein the case assembly comprises the cooling fan within the storage chamber.

28. The portable sanitizing system of claim 26, wherein the case assembly comprises the one or more batteries within the storage chamber.

29. The portable sanitizing system of claim 26, wherein the case assembly comprises the power supply within the storage chamber.

30. The portable sanitizing system of claim 26, wherein the UV lamp is configured to emit the UV light having a wavelength between 200 nm-230 nm to disinfect a surface.

31. The portable sanitizing system of claim 26, wherein the UV lamp is configured to emit the UV light having a wavelength of 222 nm to disinfect a surface.

32. The portable sanitizing system of claim 26, wherein the UV lamp is configured to emit the UV light having a wavelength between 230 nm-280 nm to disinfect a surface.

33. The portable sanitizing system of claim 26, wherein the UV lamp is configured to emit the UV light having a wavelength of 254 nm to disinfect a surface.

\* \* \* \* \*